US011020045B2

(12) United States Patent
Filloux et al.

(10) Patent No.: US 11,020,045 B2
(45) Date of Patent: *Jun. 1, 2021

(54) SYSTEMS AND METHODS FOR EVALUATING THE INTEGRITY OF A UTERINE CAVITY

(71) Applicant: MINERVA SURGICAL, INC., Redwood City, CA (US)

(72) Inventors: Dominique Filloux, Redwood City, CA (US); Dave Clapper, Atherton, CA (US); Eugene Skalnyi, Hillsborough, CA (US); Akos Toth, Cupertino, CA (US); Sean Darby, San Jose, CA (US); Tejas N. Mazmudar, Palo Alto, CA (US); Estela Hilario, Los Altos, CA (US)

(73) Assignee: Minerva Surgical, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/954,491

(22) Filed: Apr. 16, 2018

(65) Prior Publication Data

US 2018/0263550 A1    Sep. 20, 2018

Related U.S. Application Data

(63) Continuation-in-part of application No. PCT/US2018/015774, filed on Jan. 29, 2018.
(Continued)

(51) Int. Cl.
*A61B 5/00*   (2006.01)
*A61B 18/14*  (2006.01)
(Continued)

(52) U.S. Cl.
CPC .......... *A61B 5/4325* (2013.01); *A61B 5/4836* (2013.01); *A61B 18/042* (2013.01);
(Continued)

(58) Field of Classification Search
None
See application file for complete search history.

(56) References Cited

U.S. PATENT DOCUMENTS

| 737,131 A | 8/1903 | Frederick |
| 3,948,259 A | 4/1976 | Bolduc et al. |

(Continued)

FOREIGN PATENT DOCUMENTS

| WO | WO-2016057545 A1 | 4/2016 |
| WO | WO-2018140892 A1 | 8/2018 |

OTHER PUBLICATIONS

Office Action dated Mar. 23, 2017 for U.S. Appl. No. 15/418,635.
(Continued)

*Primary Examiner* — Patrick Fernandes
*Assistant Examiner* — Benjamin S Melhus
(74) *Attorney, Agent, or Firm* — Wilson Sonsini Goodrich & Rosati

(57) ABSTRACT

A system for accessing a patient's uterine cavity and detecting perforations in the uterus includes an elongated probe having a flow channel extending to a terminal outlet in a distal region of the probe. A fluid source is coupled to the flow channel, and a seal on the probe is positionable in an endocervical canal. The probe may be trans-cervically inserted into the uterine cavity, and a fluid may be introduced through the channel to flow outwardly from the terminal outlet into the uterine cavity. A parameter of said fluid flow is monitored to detect a perforation in the uterus.

20 Claims, 16 Drawing Sheets

Related U.S. Application Data

(60) Provisional application No. 62/473,049, filed on Mar. 17, 2017.

(51) Int. Cl.
*A61M 13/00* (2006.01)
*A61B 18/04* (2006.01)
*A61B 18/00* (2006.01)
*A61B 90/00* (2016.01)

(52) U.S. Cl.
CPC ....... *A61B 18/1485* (2013.01); *A61M 13/003* (2013.01); *A61B 5/6847* (2013.01); *A61B 2018/0063* (2013.01); *A61B 2018/00214* (2013.01); *A61B 2018/00559* (2013.01); *A61B 2018/00577* (2013.01); *A61B 2018/00863* (2013.01); *A61B 2018/00904* (2013.01); *A61B 2090/064* (2016.02); *A61M 2202/0225* (2013.01); *A61M 2205/3334* (2013.01); *A61M 2210/1433* (2013.01)

(56) References Cited

U.S. PATENT DOCUMENTS

| | | | |
|---|---|---|---|
| 4,979,948 A | 12/1990 | Geddes et al. | |
| 5,191,883 A | 3/1993 | Lennox et al. | |
| 5,769,880 A | 6/1998 | Truckai et al. | |
| 5,776,129 A | 7/1998 | Mersch | |
| 5,827,273 A | 10/1998 | Edwards | |
| 5,891,134 A | 4/1999 | Goble et al. | |
| 5,925,038 A | 7/1999 | Panescu et al. | |
| 6,041,260 A | 3/2000 | Stern et al. | |
| 6,296,639 B1 | 10/2001 | Truckai et al. | |
| 6,508,815 B1 | 1/2003 | Strul et al. | |
| 6,554,780 B1* | 4/2003 | Sampson | A61B 18/00 600/560 |
| 6,663,626 B2 | 12/2003 | Truckai et al. | |
| 6,736,811 B2 | 5/2004 | Panescu et al. | |
| 6,813,520 B2 | 11/2004 | Truckai et al. | |
| 7,371,231 B2 | 5/2008 | Rioux et al. | |
| 8,197,476 B2 | 6/2012 | Truckai | |
| 8,197,477 B2 | 6/2012 | Truckai | |
| 8,343,878 B2 | 1/2013 | Qiu et al. | |
| 8,372,068 B2 | 2/2013 | Truckai | |
| 8,382,753 B2 | 2/2013 | Truckai | |
| 8,394,037 B2 | 3/2013 | Toth | |
| 8,500,732 B2 | 8/2013 | Truckai et al. | |
| 8,540,708 B2 | 9/2013 | Truckai et al. | |
| 8,690,873 B2 | 4/2014 | Truckai et al. | |
| 8,821,486 B2 | 9/2014 | Toth et al. | |
| 8,939,971 B2 | 1/2015 | Truckai et al. | |
| 9,050,102 B2 | 6/2015 | Truckai | |
| 9,662,060 B2* | 5/2017 | Peliks | A61B 5/4325 |
| 10,213,151 B2 | 2/2019 | Filloux et al. | |
| 2003/0060800 A1 | 3/2003 | Ryan | |
| 2004/0116955 A1* | 6/2004 | Foltz | A61M 29/02 606/193 |
| 2005/0143728 A1 | 6/2005 | Sampson et al. | |
| 2005/0240211 A1* | 10/2005 | Sporri | A61B 17/42 606/193 |
| 2007/0088344 A1 | 4/2007 | Schechter et al. | |
| 2008/0097425 A1 | 4/2008 | Truckai | |
| 2008/0167664 A1 | 7/2008 | Payne et al. | |
| 2009/0054892 A1 | 2/2009 | Rioux et al. | |
| 2010/0198214 A1* | 8/2010 | Layton, Jr. | A61B 17/42 606/33 |
| 2010/0228239 A1* | 9/2010 | Freed | A61B 18/1485 606/27 |
| 2013/0310705 A1* | 11/2013 | Toth | A61B 5/035 600/560 |
| 2015/0173826 A1 | 6/2015 | Churchill et al. | |
| 2015/0289920 A1 | 10/2015 | Burnett et al. | |
| 2015/0366607 A1 | 12/2015 | Bek et al. | |
| 2016/0331444 A1 | 11/2016 | Truckai et al. | |
| 2019/0142331 A1 | 5/2019 | Filloux et al. | |

OTHER PUBLICATIONS

Office Action dated Jun. 14, 2017 for U.S. Appl. No. 15/418,635.
PCT/US2018/015774 International Search Report dated May 30, 2018.
U.S. Appl. No. 15/418,635 Office Action dated Jan. 17, 2018.
"Notice of allowance dated Dec. 6, 2018 for U.S. Appl. No. 15/418,635".
"Office Action dated Jun. 29, 2018 for U.S. Appl. No. 15/418,635.".

* cited by examiner

SYSTEMS AND METHODS FOR EVALUATING THE INTEGRITY OF A UTERINE CAVITY

CROSS-REFERENCE TO RELATED APPLICATIONS

This application is a continuation-in-part of PCT Application No. PCT/US2018/015774, filed Jan. 29, 2018, which claims the benefit of (1) U.S. patent application Ser. No. 15/418,635, filed Jan. 27, 2017, and (2) Provisional No. 62/473,049, filed Mar. 17, 2017, the entire contents of which are incorporated herein by reference.

This application is also a continuation-in-part of U.S. patent application Ser. No. 15/418,635, filed Jan. 27, 2017, the entire content of which is incorporated herein by reference.

BACKGROUND OF THE INVENTION

1. Field of the Invention

The present invention relates to systems and methods for global endometrial ablation in a treatment of menorrhagia. More particularly, the present invention relates to a subsystem using gas flows and a controller to test whether a patient's uterine cavity has a wall that is perforated or whether the uterus is intact, wherein such a test should be performed before proceeding with an ablation procedure.

A variety of devices have been proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811; 5,925,038 show an inflatable conductive electrode.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods, systems and devices for evaluating the integrity of a uterine cavity. The uterine cavity may be perforated or otherwise damaged by the transcervical introduction of probes and instruments into the uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate. If the flow rate drops to zero or close to zero, this indicates that the uterine cavity is intact and not perforated. If the flow rate does not drop to zero or close to zero, this indicates that a fluid flow is leaking through a perforation in the uterine cavity into the uterine cavity or escaping around an occlusion balloon that occludes the cervical canal.

Embodiments herein provide a method of characterizing a patient's uterus, which can comprise introducing a flow of a fluid into a uterine cavity of a patient and monitoring the flow to characterize the uterine cavity as at least one of perforated or non-perforated based on a change in a rate of the flow. The introducing step may include, for example, trans-cervically introducing a probe into the uterine cavity and introducing the flow through the probe.

Monitoring may include providing a signal, responsive to the rate of flow, that characterizes the uterine cavity as at least one of perforated or non-perforated. As an example, monitoring may include generating a signal responsive to the rate of flow not dropping below a predetermined level, the signal characterizing the uterine cavity as perforated. In embodiments, the predetermined level may be in the range of 0.01 slpm to 1.0 slpm, and more often between 0.01 splm, and 0.05 slpm.

In embodiments, monitoring comprises generating a signal responsive to the rate of flow dropping below a predetermined level, the signal characterizing the uterine cavity as non-perforated. The predetermined level may be, for example, 0.02 slpm.

In further embodiments, monitoring comprises monitoring a rate of flow after a predetermined first interval after initiation of the flow. The first interval may be, as examples, at least 5 seconds, at least 15 seconds, or at least 30 seconds.

Monitoring may additionally include monitoring a rate of flow over a second predetermined interval after the first interval. The second interval may be a least 1 second, at least 5 seconds, or at least 10 seconds, as examples.

In additional embodiments, monitoring includes providing a signal, responsive to the rate of flow, that characterizes the uterine cavity as at least one of perforated or non-perforated, and wherein the signal is at least one of visual, aural and tactile.

In embodiments, prior to introducing the flow, a member is positioned within the cervical canal that substantially prevents a flow of the fluid out of the uterine cavity. Introducing may include transcervically introducing a probe into the uterine cavity, and introducing the flow through the probe, with the member positioned about an exterior of the probe. The member may be expanded in the cervical canal.

In embodiments, the fluid is a gas or a liquid.

In additional embodiments, introducing includes transcervically introducing a probe into the uterine cavity, and introducing the flow through the probe. The probe has a working end with an energy-delivery surface for ablating uterine cavity tissue. Responsive to the uterine cavity being characterized as perforated, energy delivery surface is disabled. Alternatively or additionally, responsive to the uterine cavity being characterized as non-perforated, activation of the energy delivery surface may be enabled or even caused to happen automatically.

In embodiments, a method of endometrial ablation is provided, the method including introducing an ablation probe into a uterine cavity of a patient, flowing a fluid from a fluid source through the probe into the uterine cavity, monitoring the rate of the flow of the fluid into the uterine cavity to characterize the cavity as at least one of perforated or non-perforated based on a change in the flow rate, and responsive the to the uterine cavity being characterized as non-perforated, activating the ablation probe to ablate an interior of the uterine cavity.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 7A is a schematic view of another variation of a system and method of the invention that monitors uterine integrity, wherein the elongated probe functions as a sound for measuring uterine cavity length while at the same time using fluid flows through the probe as in previous embodiments, wherein FIG. 7A depicts a non-perforated uterine cavity.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiments being described.

In general, an endometrial ablation system is described herein that comprises an elongated introducer member for accessing a patient's uterine cavity with a working end that deploys an energy applicator comprising an expandable thin-wall dielectric structure adapted to contain a gas. In one variation, an interior chamber of the thin-wall dielectric structure or array contains a circulating neutral gas such as argon. An RF power source provides current that is coupled to the neutral gas flow by a first polarity electrode disposed within the interior chamber and a second polarity electrode at an exterior of the dielectric structure. The circulating gas flow, which is converted to a conductive plasma within the array by the electrode arrangement, permits current flow through engaged endometrial tissue only when the voltage across the combination of the then-ionized gas or plasma, the thin-wall dielectric structure and the engaged tissue reaches a threshold that causes capacitive coupling across the thin-wall dielectric material. The conductive plasma heats the dielectric wall which in turn conducts heat to the tissue in contact with the array. This electrosurgical ablation system is described in more detail in the following commonly owned and/or licensed U.S. Pat. Nos. 9,050,102; 8,939,971; 8,821,486; 8,690,873; 8,540,708; 8,500,732; 8,382,753; 8,372,068; 8,343,878; 8,197,477 and 8,197,476, all of which are incorporated herein by this reference.

Figure 1:
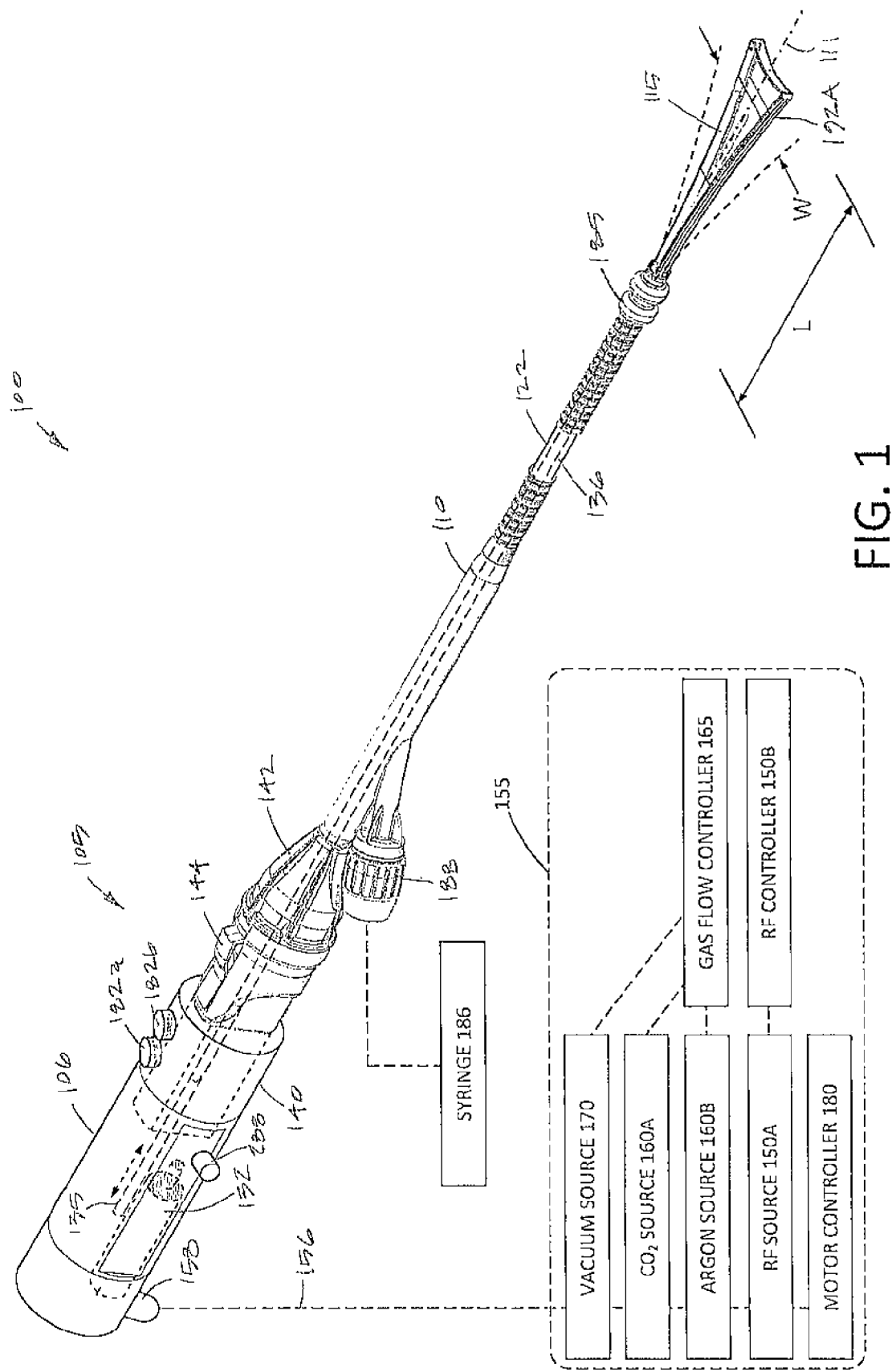
FIG. 1 is a perspective view of an ablation system corresponding to the invention, including a hand-held electrosurgical device for endometrial ablation and a block diagram showing an RF power source, an RF controller, a $CO_2$ gas source, an argon gas source, a gas flow controller and an electrical source and controller for a motor carried by the hand-held device.

FIG. 1 depicts one embodiment of an electrosurgical ablation system 100 configured for endometrial ablation. The system 100 includes a hand-held device 105 with a proximal handle 106 shaped for grasping with a human hand that is coupled to an elongated shaft or introducer 110 extending about longitudinal axis 111 to a distal portion that comprises an energy applicator or expandable body 115. The introducer 110 can be fabricated of a thin-wall plastic, composite or metal in a round or oval cross-section having a diameter or major axis ranging from about 3 mm to 8 mm and a length suited for trans-cervical access to a patient's uterine cavity. The handle 106 is shown in an in-line configuration in FIG. 1, but any type of pistol grip or other handle design is possible.

Figure 2:
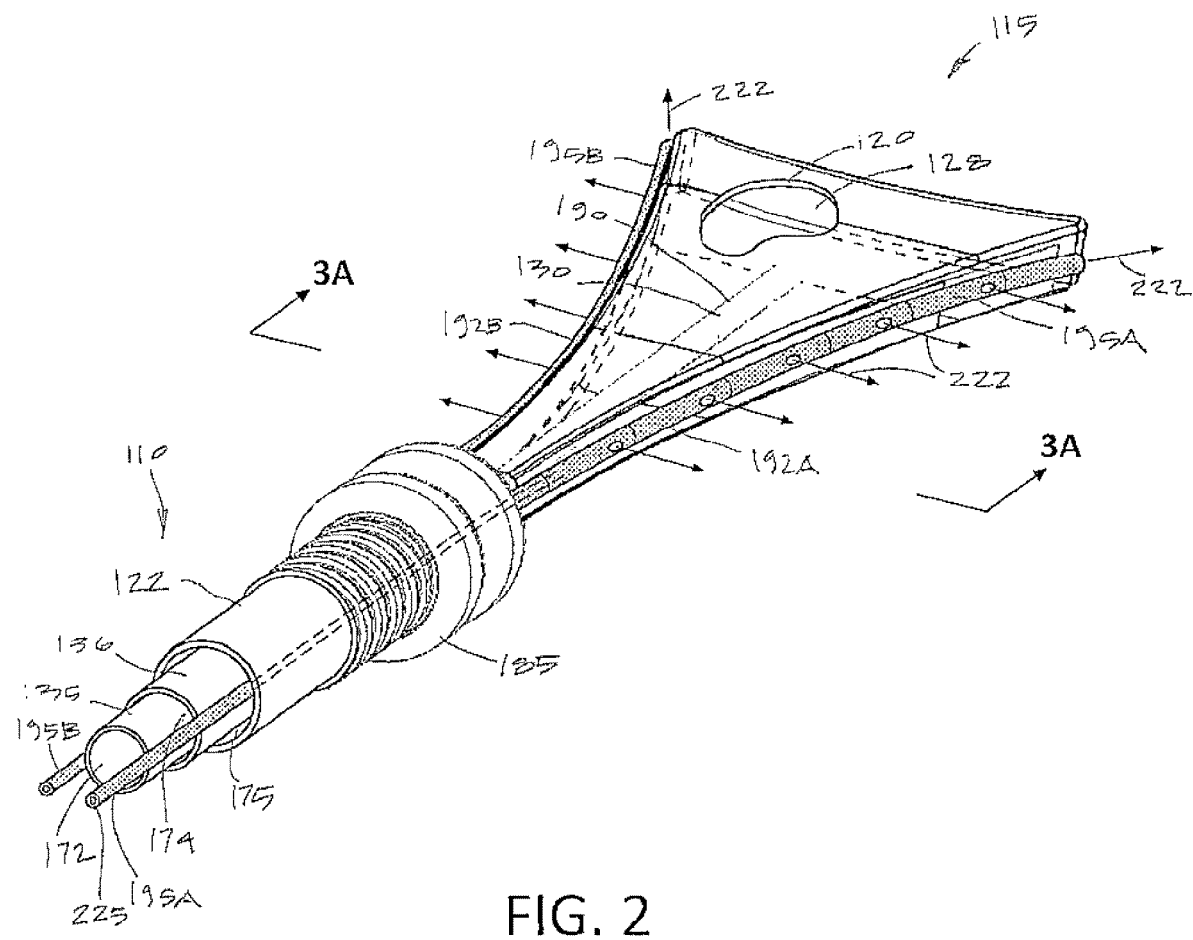
FIG. 2 is a perspective view of the distal energy applicator or working end of the hand-held electrosurgical device of FIG. 1 with the energy applicator comprising an expanded thin-wall dielectric structure including flow channels extending along sides of the dielectric structure.

Referring to FIG. 2, the energy applicator 115 consists of a structure comprising a flexible or elastomeric thin wall material 120 that can be expanded to a range of triangular shapes as indicated by phantom shape 125 of FIG. 1. The thin wall 120 is a dielectric material and can be collapsed or constrained at least partially within an outer sleeve 122 of the introducer 110. Such a triangular shape is configured for substantially contacting the endometrial lining of a patient's uterus that is targeted for ablation. In one variation, the energy applicator 115 comprises a thin wall silicone material having a thickness ranging between 0.005" and 0.020" surrounding a fluid-tight interior chamber 128. The energy applicator 115 can be expanded to a range of widths wherein the width W in FIG. 1 shows a pre-expanded width. The expansion mechanism for expanding the energy applicator 115 can be an expandable-collapsible frame structure 130 as described in U.S. Pat. No. 9,050,102 referenced above. In the embodiment shown in FIG. 1, an electrical motor 132 is provided to actuate the expandable-collapsible frame 130 (partially shown) in interior chamber 128, which differs from the embodiment of U.S. Pat. No. 9,050,102 referenced above. The motor 132 of FIG. 1 is utilized to move a first inner sleeve 135 relative to second inner sleeve 136 (see FIG. 2) to expand or collapse the frame 130 and energy applicator 115. It can be easily understood that the motor 132 can be coupled to a gear reduction mechanism and a linear drive mechanism (not shown) to actuate the expandable-collapsible frame that is described in U.S. Pat. No. 9,050,102 and the other commonly-owned patents referenced above.

In FIG. 1, the handle 106 can be fabricated of an electrically insulative material such as a molded plastic with first and second portions, 140 and 142, wherein the second portion 142 is coupled to outer sleeve 122. It can be seen that second portion 142 is slidable relative to axis 111 into first portion 140 of handle 106. A latching mechanism 144 is adapted to lock the first and second handle portions 140 and 142 in a selected axial relationship. By this means, the outer sleeve 122 of the introducer 110 can be axially translated relative to concentric inner sleeves 135 and 136 (see FIG. 2) that carry the frame 130 and energy applicator 115 to thereby provide a selected length L (see FIG. 1) of the energy applicator 115 when expanded in a uterine cavity.

FIG. 1 further shows that the system 100 includes an RF energy source 150A and RF controller 150B in a console or control unit 155. The RF energy source 150A is connected to the hand-held device 105 by a flexible conduit 156 with a plug-in connector 158 that carries electrical leads that couple to an electrode arrangement in the applicator head or energy applicator 115 as described in detail in U.S. Pat. No. 9,050,102 referenced above. The control unit 155 is further adapted to carry first and second fluid or gas sources 160A, 160B and a gas flow controller 165 for controlling gas flows. The first fluid or gas source 160A can be a $CO_2$ cartridge which provides a $CO_2$ flow to flow channels at the surface of the energy applicator 115 for testing the integrity and non-perforation of the walls of the uterine cavity as will be described below. The second gas source 160B is an argon gas cartridge which provides the neutral gas for circulating in interior chamber 128 of the dielectric structure that is ionized into a plasma as described in detail in U.S. Pat. No. 9,050,102 referenced above. The gas flow controller 165 is further configured to control a vacuum or negative pressure source 170 in communication with the interior chamber 128 of the energy applicator, and optionally to the exterior of the energy applicator 115. The fluid flow pathways in the system include flow channels in the conduit 156 that extends from the control unit 155 to the hand-held device 105. The flow channels and pathways in the elongate introducer 110 are indicated at 172, 174 and 175 in FIG. 2. Flow channels 174 and 172 provide gas inflows and outflows, respectively, to and from the interior chamber 128 of the energy applicator 115. Flow channel 175 is adapted for providing a pathway to or from the uterine cavity around an exterior of the energy applicator 115, for example the removal of gas or liquid from the uterine cavity.

Still referring to FIG. 1, the console or control unit 155 includes a motor electrical source/controller 180 for operating the motor 132 to actuate the expandable-collapsible frame 130. In one variation, the handle 106 has first and second actuator buttons 182a and 182b for expanding and collapsing, respectively, the frame 130 in the interior of the energy applicator 115. It should be appreciated that any type of joystick, rocker switch, trigger, foot pedal or the like may be used to actuate the expandable-collapsible frame and energy applicator 115.

FIGS. 1 and 2 further show a cervical sealing balloon 185 extending along a length of the introducer 110. As can be seen in FIG. 1, the block diagram includes a syringe 186 that can be coupled to fitting 188 and the handle 106 and is adapted for inflating the expandable sealing balloon 185 as described further below.

Now turning to the electrosurgical aspects of the invention, referring again to FIG. 2, the energy applicator 115 is of the type described in detail in U.S. Pat. No. 9,050,102 and other commonly owned patents referenced above. FIG. 2 illustrates the energy applicator 115 and a cut-away view of the introducer 110 and concentric sleeve assembly thereof. The frame 130 (partially shown) in the interior chamber 128 of the energy applicator 115 comprises a first polarity electrode 190. The energy applicator 115 carries exterior or second polarity electrodes 192A and 192B extending along the sides of the triangular shaped applicator body. The opposing polarity electrodes at the interior and exterior of the dielectric structure (190 and 192A-192B) are configured to convert a flow of neutral gas in chamber 128 into a plasma and to allow capacitive coupling of current through the thin dielectric wall 120 of the applicator body.

Figure 3A:
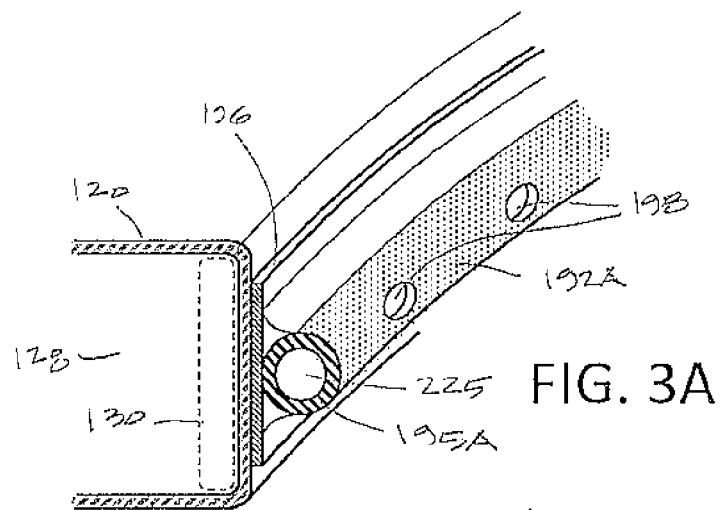
FIG. 3A is an enlarged cut-away view of a side of dielectric structure and a flow channel further depicting an electrode surface.

In the variation shown in FIGS. 1 and 2, the exterior electrodes 192A and 192B consist of a conductive electroless plating on flow channel sleeves 195A and 195B that are used to supply $CO_2$ inflows into a patient's uterine cavity to test for uterine wall perforations as will be described further below. FIG. 3A shows an enlarged sectional view of flow channel sleeve 195A of FIG. 2 wherein the sleeve is bonded to insulator layer 196 with adhesive layer 197. The insulator layer 196 can be Kapton® tape, which in turn is bonded to the thin dielectric wall 120 of the applicator body 115. A plurality of flow outlets 198 are provided along the length of the flow channel sleeves. Such flow outlets can be oriented to face laterally and/or upward and downward along the length thereof, as laterally facing flow channels may be pressed into tissue and occluded.

Figure 3B:
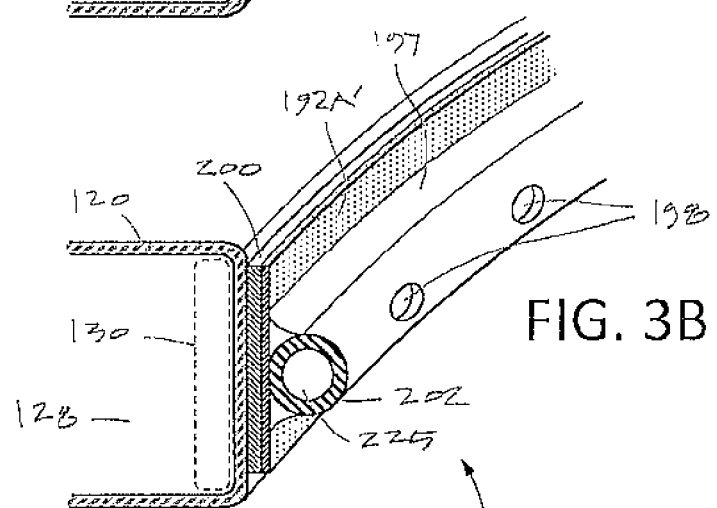
FIG. 3B is an enlarged cut-away view of the dielectric structure similar to that of FIG. 3A showing another variation of a flow channel and electrode arrangement.
Figure 3C:
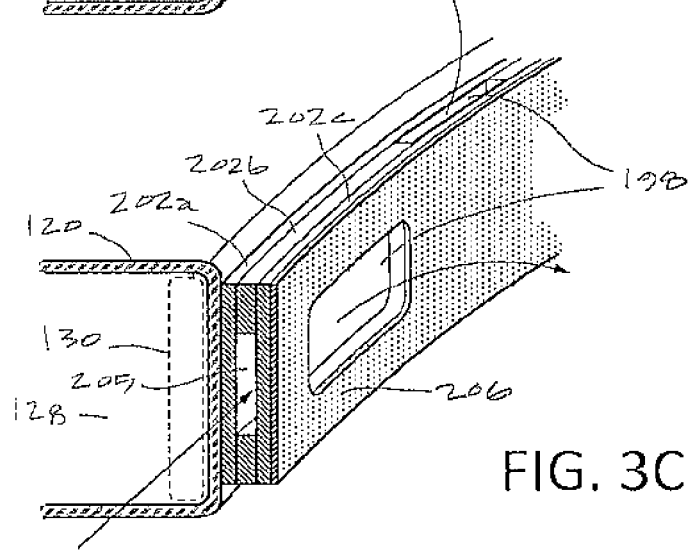
FIG. 3C is another cut-away view of the dielectric structure similar to that of FIGS. 3A-3B showing yet another variation of a flow channel and electrode arrangement.

FIGS. 3B and 3C illustrate other assemblies that provide a flow channel and electrode along an edge of the applicator body 115. FIG. 3B shows the edge of the thin dielectric wall 120 with the Kapton® insulator tape 200 bonded to the exterior of the wall. In this variation, the insulator tape 200 has a conductive plating that comprises the second polarity electrode 192A'. A separate small diameter polymer flow channel sleeve 202 is then bonded with adhesive 197 to the surface of the insulator tape 198 and electrode layer 192A'. FIG. 3C shows an alternative embodiment in which layers of insulator tape 202a, 202b and 202c are bonded to one another with an interior channel in 205 in the middle of the tape assembly that provides the interior flow channel 205. An electrode surface layer 206 is provided over the insulator layers 202a-202c. In this variation, flow outlets 198 are shown facing both laterally and upwardly. Such as assembly also can be constructed of a flexible PCB (printed circuit board).

Still referring to FIG. 2, as described further below, the tubular flow channel sleeves 195A and 195B are multi-functional and are further utilized for testing for a perforation in a patient's uterine wall. Each flow channel sleeve 195A and 195B in this variation has a plurality of outlets 198 as mentioned above along the length of each sleeve and a terminal outlet 210 at the distal end of each sleeve. As shown in FIG. 2, the flow channel sleeves 195A and 190B extend proximately through the interior of introducer 110 and communicate with the $CO_2$ source 160A (see FIG. 1). Thus, it can be seen that $CO_2$ flows indicated by arrows 222 in FIG. 2 can exit the outlets 198 and 210 into a patient's uterine cavity 224 after deployment of the energy applicator 115. The flow pathway 225 in each sleeve 195A and 195B (see FIG. 2) can have a diameter or mean cross-section ranging between about 0.01 mm and 1.0 mm.

In general, the system and methods of the invention allow for the evaluation of the integrity of the patient's uterine cavity which may be perforated or otherwise damaged by the transcervical introduction of probes, sounds and/or other instruments into a uterine cavity. If the uterine wall is perforated, it would be preferable or necessary to defer any ablation treatment until the uterine wall is healed. Thus, a method described in U.S. Pat. No. 8,343,078 and in the other commonly-owned patents referenced above, consists of introducing trans-cervically an introducer into a patient's uterine cavity, expanding a sealing balloon in the endocervical canal, providing a flow of a fluid (e.g., $CO_2$) through the introducer into the uterine cavity and monitoring one or more parameters of the $CO_2$ flow which allow for characterization of the uterine cavity as either perforated or non-perforated based on an evaluation of a selected gas flow parameter.

Figure 4:
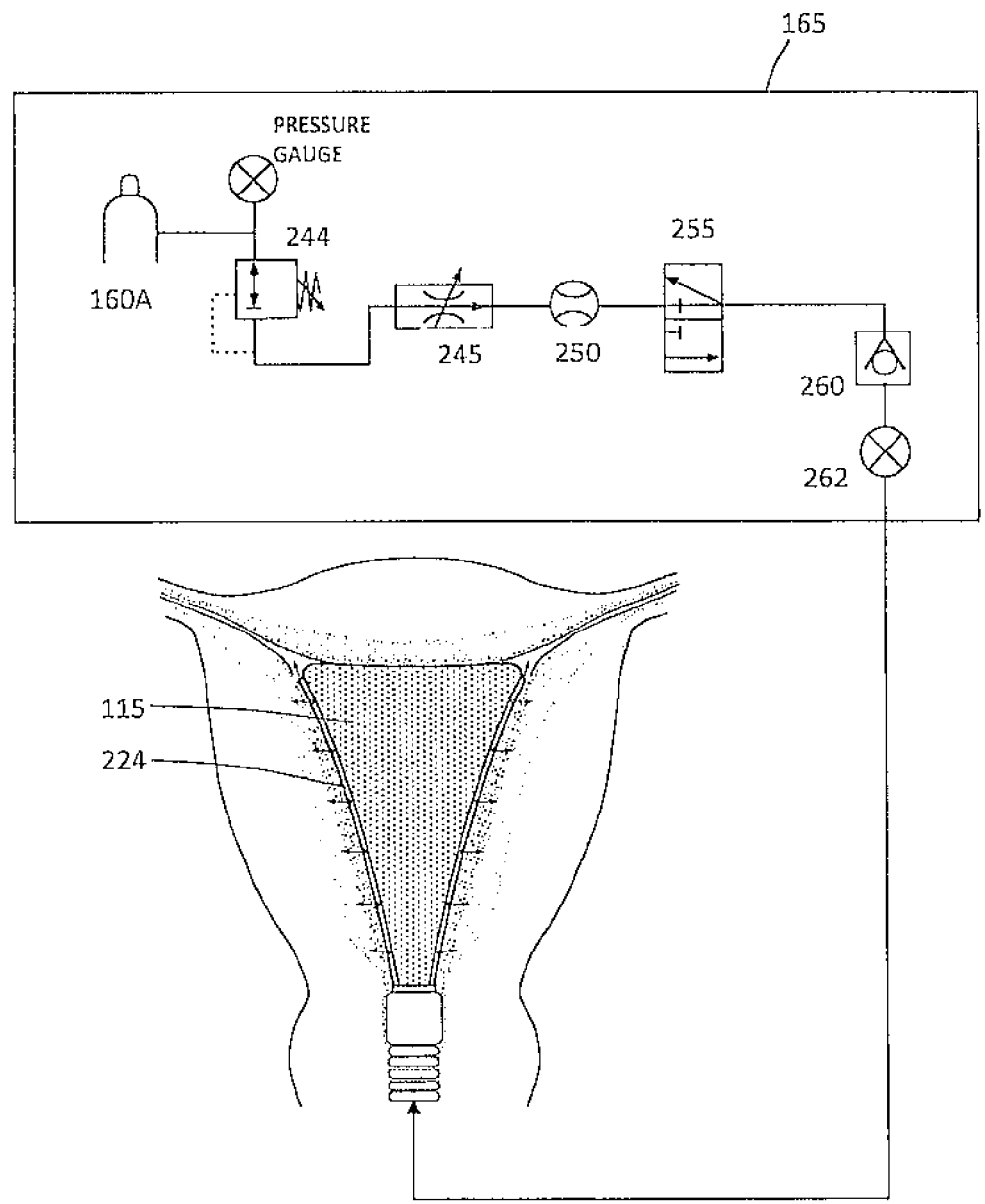
FIG. 4 is a block diagram of the gas flow components of the controller unit of FIG. 1.

FIG. 4 is a block diagram that schematically depicts the system components that are related to the cavity integrity test subsystem only. These components include the gas flow controller 165 that provides the flow of $CO_2$ through the hand-held probe 105 and introducer 110 to flow channel sleeves 195A and 195B (FIG. 2) and the pressurized $CO_2$ source 240, which can be a disposable $CO_2$ canister. The $CO_2$ source 240 communicates with a downstream pressure regulator 244, an optional proportional valve 245, a flow meter 250, a normally closed solenoid valve 255 and one-way valve 260 for preventing venting of $CO_2$ through valve 255. Upon actuation or the valve 255 by the physician, a flow of $CO_2$ gas can be provided from $CO_2$ source 240 at a predetermined flow rate and pressure through the hand-held device 105 and into the uterine cavity 224. As will be described below, the controller can have control algorithms to monitor the flow rate with flowmeter 250 to determine whether there is a perforation in a wall of the uterine cavity. Alternatively, the pressure sensor 262 shown in FIG. 4 can be used to test for perforations as is known in the art.

Figure 5B:
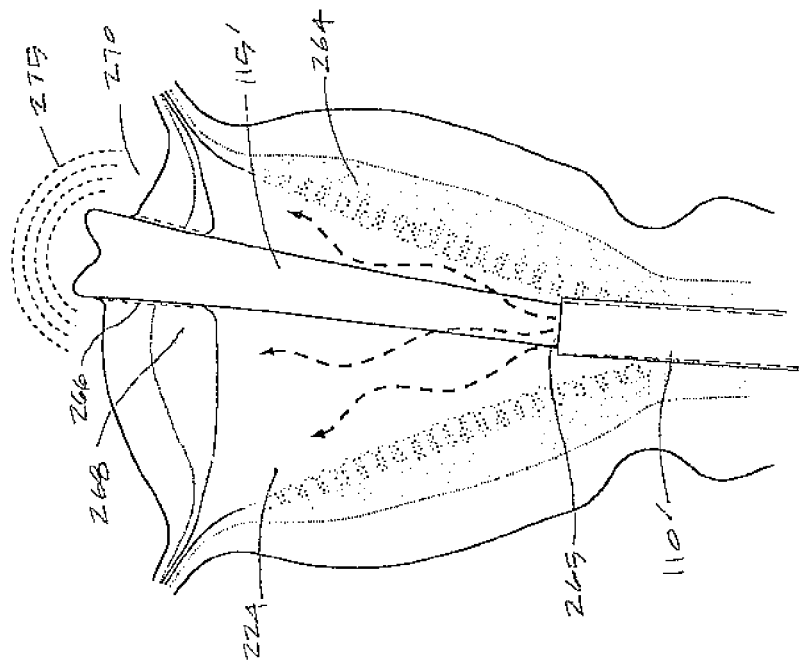
FIG. 5B is a schematic view of a prior art method of testing uterine integrity similar to that of FIG. 5A, except FIG. 5B indicates that the energy applicator has penetrated the fundus, and potentially plugs the perforation so that gas flow does not exit the perforation which results in characterizing the uterus as non-perforated when there is a perforation.
Figure 5A:
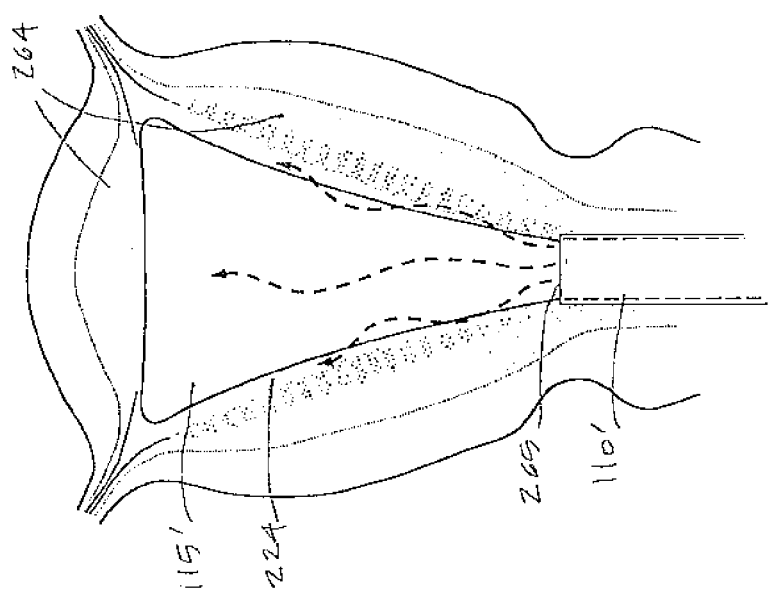
FIG. 5A is a schematic view of a prior art method of testing uterine integrity, including introducing an energy applicator into a patient's uterine cavity, expanding the energy applicator, actuating a gas flow from the introducer sleeve into the uterine cavity, and monitoring at least one gas flow parameter to determine that there is no perforation in a uterine cavity wall.

Before describing the method of using the system described above and shown in FIGS. 1 and 2, it is useful to describe a typical prior art system that has been developed for uterine perforation detection. FIGS. 5A and 5B illustrate a prior art method of testing for uterine cavity integrity and further shows the potential deficiencies in such a prior art system. In FIG. 5A, it can be seen that the prior art introducer 110' and energy applicator 115' (similar to the type shown in FIGS. 1-2) has been inserted into the uterine cavity 224 and the energy applicator 115' has been expanded. Prior to inserting the introducer 110' into the uterine cavity, the physician used an elongate probe called a uterine sound (not shown) to determine the length of the uterine cavity 224. At times, the physicians initial use of such a probe or sound can cause damage to, or perforation of, the uterine wall 264. At times, an irregular uterine shape will contribute to such damage or perforation of a uterine wall 264. Thus, a key objective of a uterine cavity integrity test is to determine whether the physicians use of a probe or sound has caused such a perforation. In FIG. 5A, it is assumed that no perforation resulted from the physician using the probe or sound. It can be seen that the $CO_2$ gas flows outwardly from the distal end 265 of the introducer 110' and fills the uterine cavity 224 around the exterior of the expanded energy applicator 115'. In this situation, the use of a flow meter, a pressure sensor or a gas volume meter can be utilized to characterize the uterine wall 264 as non-perforated as is known in the prior art.

In FIG. 5B, it is assumed that the physician's use of the probe or sound resulted in a perforation 266 in the fundus portion 268 of the uterine wall 264. Further, FIG. 5B shows that the physicians insertion of the energy applicator 115' followed the path of the sound through the perforation 265 in the fundus 268. Thereafter, the $CO_2$ gas flow is initiated in the manner described previously. In this situation, either of two things may occur. First, it is possible that $CO_2$ will escape the uterine cavity 224 around the energy applicator 115' outwardly through perforation 265 and into the uterine cavity 270, which can be detected by monitoring at least one flow parameter (flow rate, gas pressure, gas volume). Thus, the perforation 266 will be detected by the system and the physician will not proceed with the ablation procedure. However, a second outcome is possible when the energy applicator 115' effectively occludes or seals the perforation 266 since the cross-section of energy applicator 115' can effectively plug such a perforation 266. In this situation, the $CO_2$ flow outwardly from the introducer 110' into the uterine cavity would be monitored and the uterine cavity 224 could be characterized as non-perforated, when in fact there is a perforation 266. If this scenario were to occur, the further actuation of the energy applicator 115', with energy emission indicated at 275 in FIG. 5B, would likely cause thermal injury to organs within the abdominal cavity 270 outside the fundus 268. Such an injury to organs in the patient's abdominal cavity 270 could be very serious and potentially life-threatening.

Figure 6A:
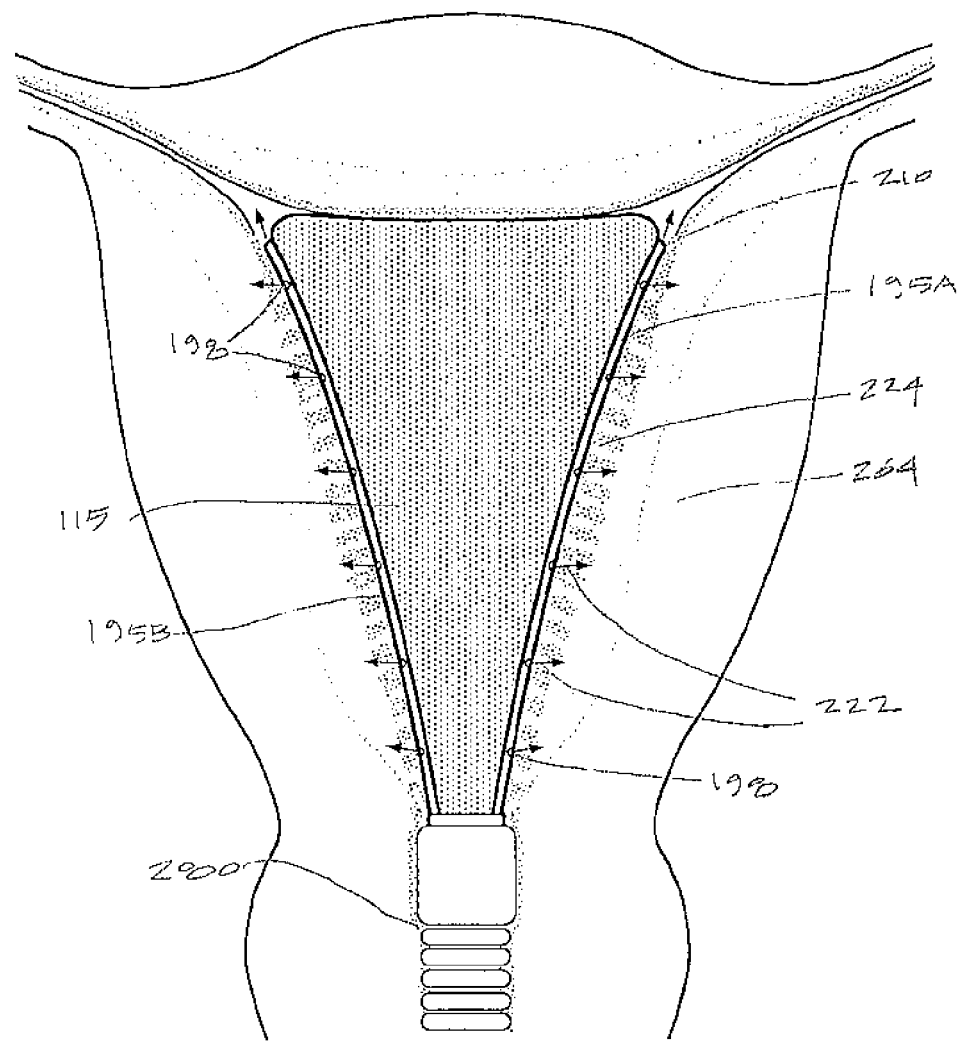
FIG. 6A is a schematic view of the system and method corresponding to the invention for testing uterine cavity integrity, wherein FIG. 6A includes steps of introducing an energy applicator into a patient's uterine cavity, expanding a sealing balloon in the endocervical canal, expanding the energy applicator, actuating a gas flow that exits the energy applicator through flow outlets along its entire length, and monitoring at least one gas flow parameter to determine that there is no perforation in a uterine cavity wall.
Figure 6B:
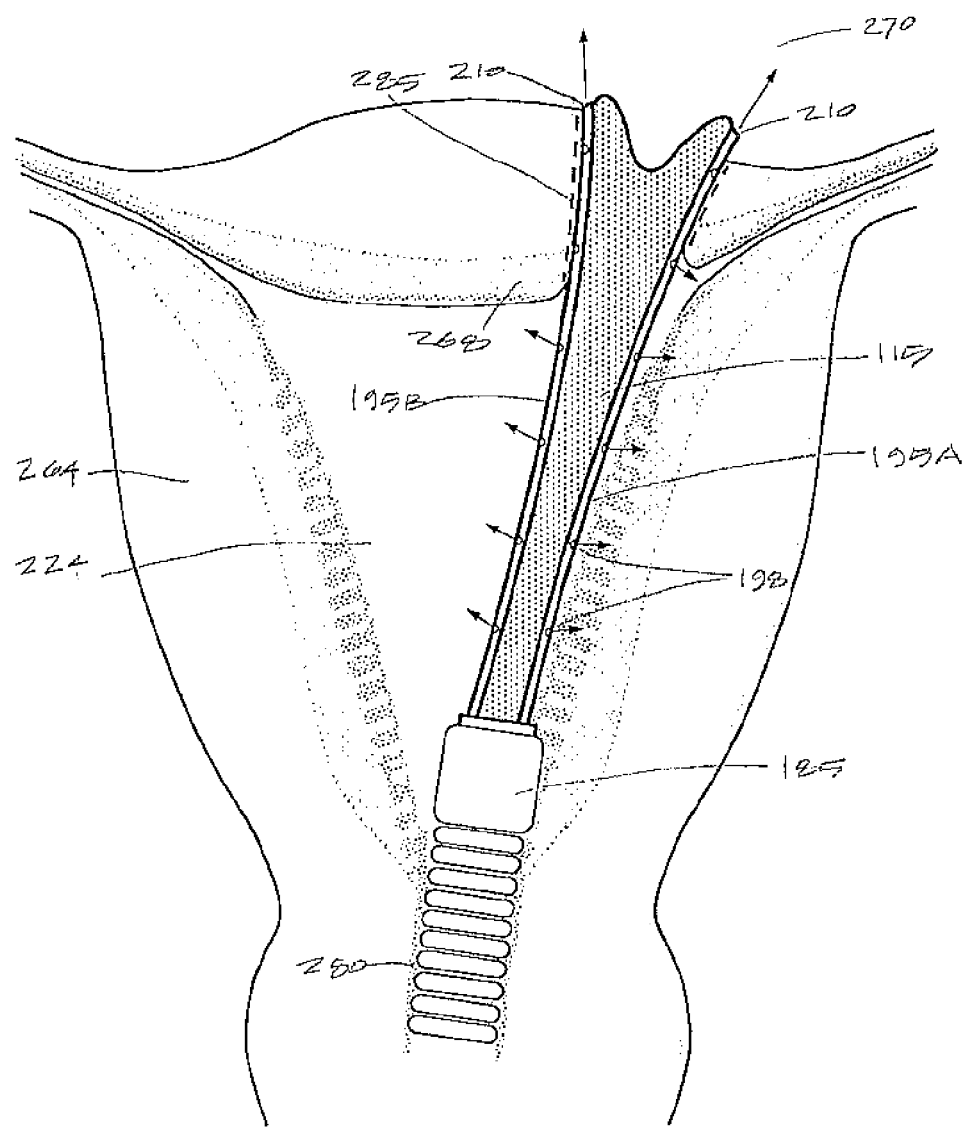
FIG. 6B is a schematic view similar to that of FIG. 6A, except that FIG. 6B indicates that the energy applicator has penetrated the fundus, and potentially plugs the perforation, except that unlike the prior art in FIG. 4B, the gas flow is directed though non-collapsible flow channels to the distal tip of the energy applicator and into the abdominal cavity, wherein monitoring at least one gas flow parameter will determine that there is a perforation in the uterine cavity wall.

FIGS. 6A-6B illustrate the improved systems and methods corresponding to the invention, which can solve the problem of mischaracterizing the integrity of the uterine cavity, which can occur with a prior art system as illustrated in FIG. 5B. In FIG. 6A, it can be seen that the energy applicator 115 of FIG. 2 is expanded in the patient's uterine cavity. Prior to insertion and expansion of the applicator body 115, the inflatable seal 185 was expanded in the endocervical canal 280. In FIG. 6A, it is again assumed that the physician has successfully used a probe or sound to measure the length of the uterine cavity 224 which resulted in no perforation of the uterine wall 264 with the sound. FIG. 6A shows $CO_2$ being introduced through the flow sleeves 195A and 190B and thereafter the $CO_2$ flows outwardly from outlets 198 and 210 into the uterine cavity 224. In one variation of monitoring a flow parameter, the physician actuates the system to electronically open valve 255 in the gas flow controller 165 which provides the $CO_2$ flow through the system. The gas flow controller 165 monitors the flow meter 250 therein over an interval that can range from 1 second to 60 seconds, or 5 second to 30 seconds, to determine the change in the rate of flow and/or a change in pressure. In an embodiment, the flow sensor 250 comprises a Honeywell AWM5000 Series Mass Airflow Sensor, for example Model AWM5101, that measure flows in units of mass flow. Other flow sensors may be used, such as a Honeywell AWM3000 or Honeywell Zephyr model sensor. In one embodiment, the initial flow rate is between 0.01 slpm (standard liters per minute) and 1.0 slpm, or between 0.01 slpm and 0.02 slpm. The gas flow controller 165 includes a microprocessor or programmable logic device that provides a feedback signal from the flow meter indicating that either (i) the flow rate has dropped to zero or close to zero to thus characterize the uterine cavity as non-perforated, or (ii) the flow rate has not dropped to a predetermined threshold level within a predetermined time interval to thus characterize the uterine cavity as perforated or that there is a failure in sealing balloon 185 or its deployment so that the cervical canal 280 is not occluded. In one embodiment, the threshold level is 0.02 slpm for characterizing the uterine cavity as non-perforated. In this embodiment, the controller provides a signal indicating a non-perforated uterine cavity if the flow drops below 0.02 slpm between a first time point, (e.g., 0.5 seconds of flow, 1 second of flow, or 2 seconds of flow) and a second time point which is a flow time-out limit, which can be 5 seconds, 10 seconds, 20 seconds or 30 seconds. If the system then characterizes the uterine cavity as non-perforated, the controller can enable actuation of energy delivery by the physician or automatically actuate energy delivery.

FIG. 6B illustrates another scenario in which the physicians use of the sound resulted in a perforation 285 in the fundus 266, similar to that depicted in use of the prior art device in FIG. 5B. Further, FIG. 6B shows that the physicians insertion of energy applicator 115 followed the path of the sound through the perforation 285 and into the abdominal 270. Thereafter, the $CO_2$ gas flow is initiated which propagates through flow channel sleeves 195A and 195B to the plurality of outlets 198 and 210 in each sleeve. As can be seen in FIG. 6B, the flow channel sleeves 195A and 190B extend over the entire length of the energy applicator 115 and it can be seen that $CO_2$ will flow (indicated by arrows 222) through some outlets 198 into the uterine cavity 224 and flow through other outlets 198 or at least terminal outlets 210 into the patient's abdominal cavity 270. In this situation, even if the cross-section of the energy applicator 115 effectively plugs the perforation 285, such a perforation will be detected easily since $CO_2$ will flow unimpeded through outlets 210 into the patient's uterine cavity 270 which offers little to no resistance to such a gas inflow. Thus, if the initial flow rate is between 0.01 slpm and 1.0 slpm, or between 0.01 slpm and 0.05 slpm, as described above, such a flow will not drop to a predetermined threshold level within a predetermined time interval as described above, and the uterine cavity 224 will be characterized as being perforated. Following the determination that there exists a perforation, the physician then will know to not perform an ablation procedure. Optionally, the controller will disable energy delivery by the system.

Now turning back to FIG. 1, it can be understood from the motor 132 is operated to expand and contract the frame 130 within the energy applicator. Another feature is provided to allow for the quick release of the engagement between the motor and the interior sleeve 135 is driven by the motor. As can be seen in FIG. 1, the quick release button 288 is provided in the handle 106 which will disengage the motor from the interior sleeve 135 thus allowing the frame 132 collapse as the energy applicator is withdrawn from the uterine cavity through the cervical canal.

In another aspect of the invention relating to the motor-operated frame 130, the controller 115 can include algorithms that monitor the voltage to the motor 132 which, in effect, can determine the resistance to opening or widening the frame 130 and the energy applicator 115 and thereafter signal the physician that there may be an abnormal resistance to opening the energy applicator. The signal can be useful in informing the physician that the energy applicator is embedded in tissue, similar to that of a perforation, which could be important information for safely performing the procedure. The signal can be provided to the position by tactile feedback or aural or video signals.

Figure 7A:
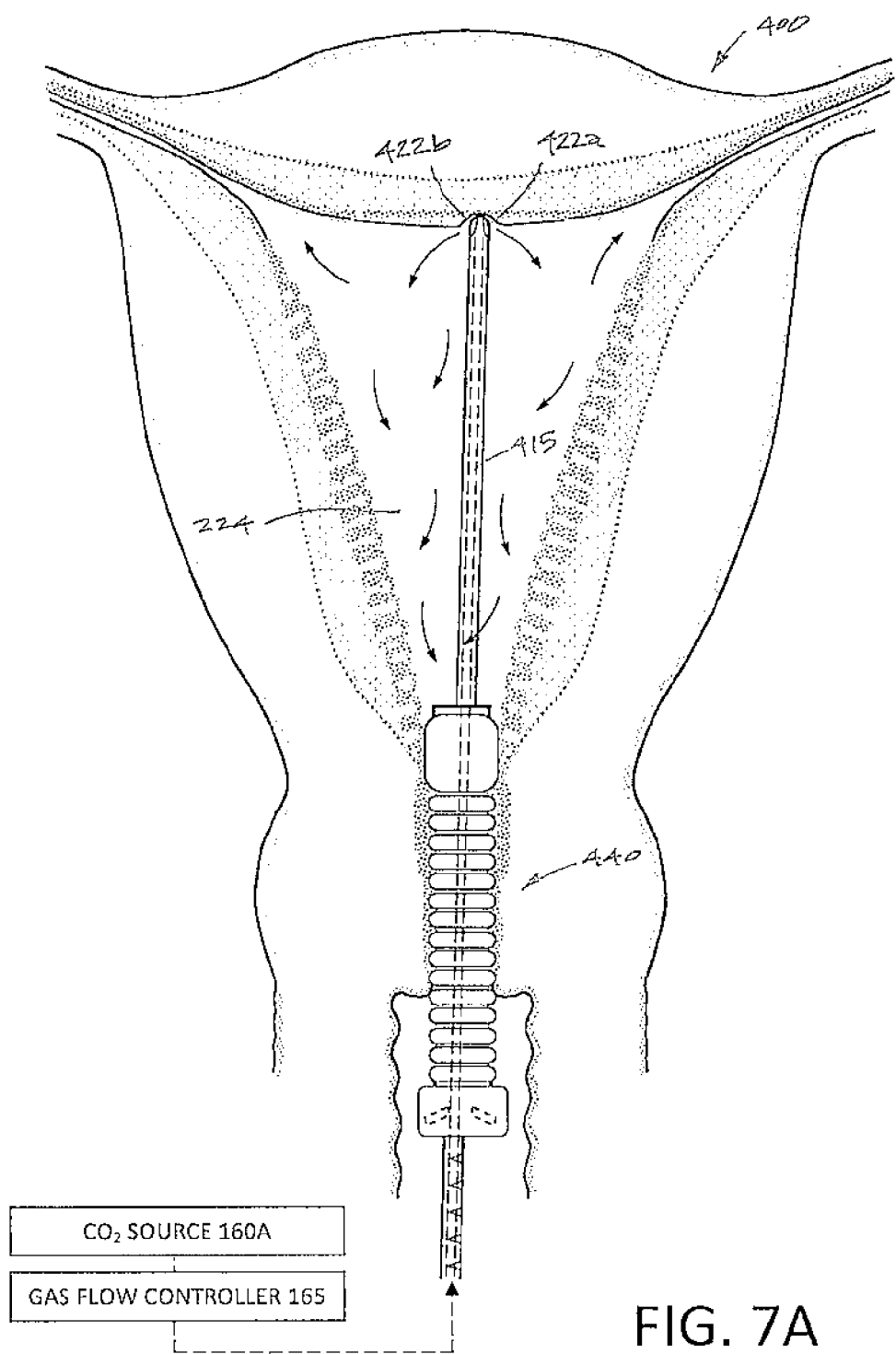
Figure 7B:
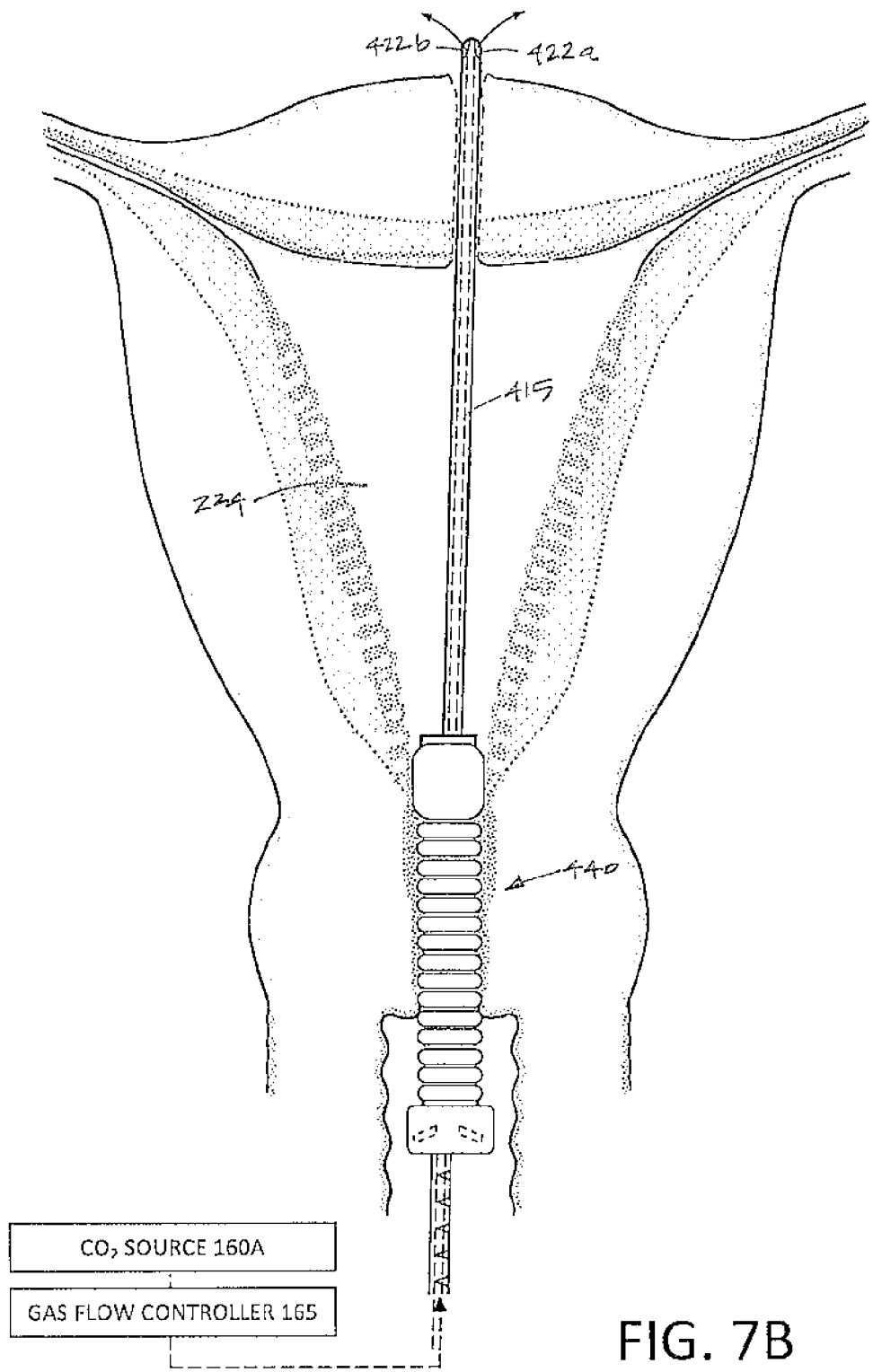
FIG. 7B is a schematic view of the probe of FIG. 7A wherein fluid flows through the probe which indicates a perforated uterine cavity.
Figure 7C:
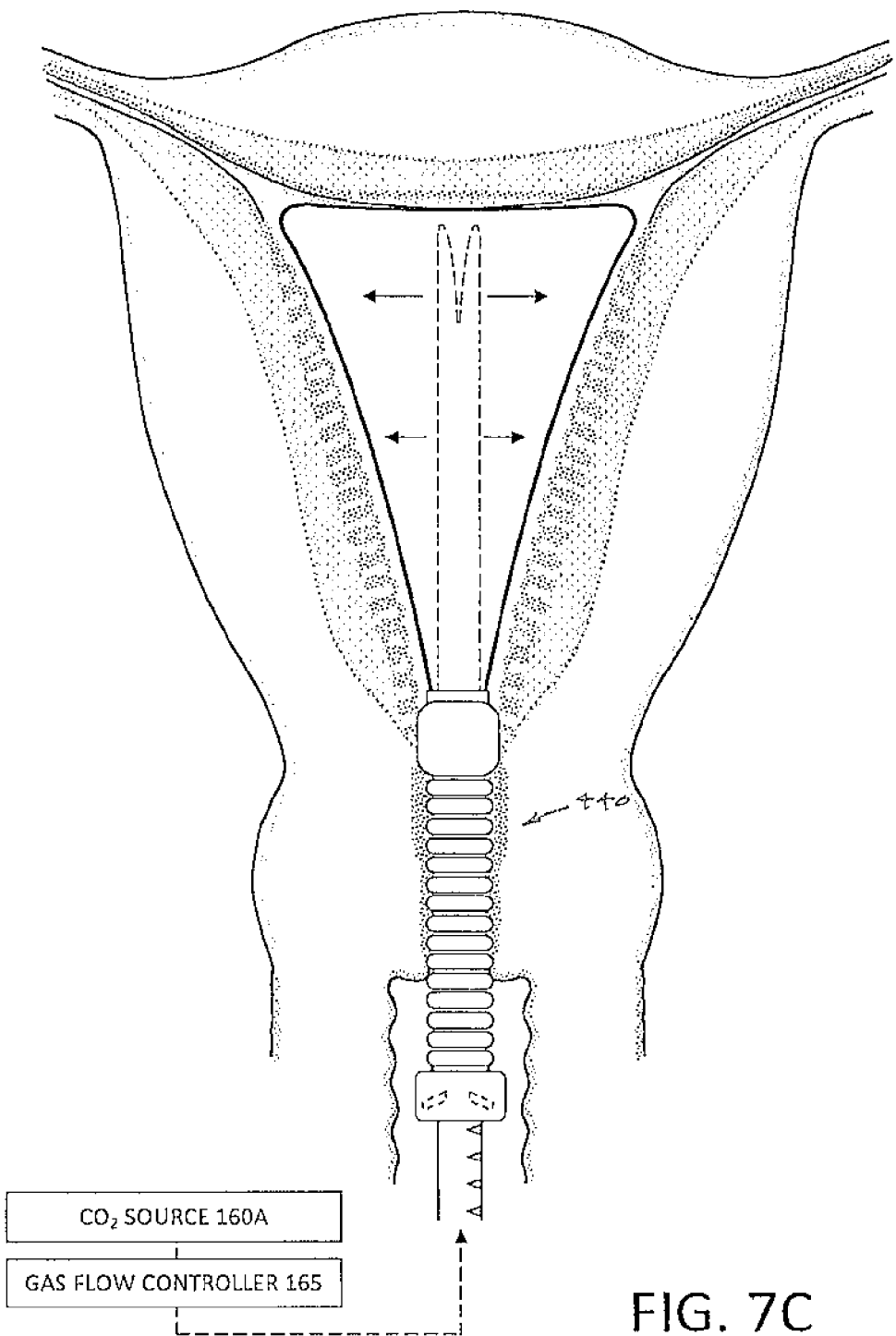
FIG. 7C is a schematic view of a step of a ablation treatment method that follows FIG. 7A wherein the measuring probe can be removed through the sealing member and an ablation probe introduced through the seal to perform an ablation procedure.

Now turning to FIGS. 7A-7C, another variation of the invention is shown which comprises an elongated probe 400 that is adapted for use as a uterine sound, or cavity length measuring device. In this variation, the probe 400 is adapted for measuring the length of the uterine cavity 224 with a dedicated instrument that does not carry an energy applicator 115. In other words, the probe 400 can be used independently in a first step or "measuring" step of the procedure, which then can be followed by a subsequent step in which an ablation device is introduced into the patient's uterine cavity to perform the ablation procedure.

In FIG. 7A, it can be seen that probe 400 has an elongated introducer portion 410 extending along axis 411 with an interior flow channel 415 therein. The flow channel 415 can be coupled to $CO_2$ source 160A and flow controller 165 as described above to provide a gas flow through flow channel 415 which extends to distal outlets 422a and 422b. In one variation, as shown in FIG. 7A, distal outlets 422a and 422b are positioned to be partially side-facing at the distal tip for 424 of the probe 400. Additional outlets can be provided near the distal tip.

FIG. 7A further shows a method using the probe 400, wherein initially a cervical sealing member 440 is positioned in the cervical canal 280. The cervical sealing member 440 can be a fluid expandable balloon as shown in FIG. 7A, or any form of resilient or foam plug as known in the prior art to substantially seal the cervical canal. The cervical sealing member 440 further includes a flexible valve, such as a duckbill valve 445 as is known in the art, for accommodating the insertion of tools therethrough while preserving a fluid seal. FIG. 7A also illustrates the step of introducing the probe 400 through the sealing member 440 into the uterine cavity 224, and providing a gas flow through fluid channel 415 which then circulates in, and expands, the uterine cavity until a preselected pressure prevents further fluid inflow. Thus, it can be understood that the controller 155 can monitor either the fluid flow rate into the uterine cavity, or the intracavity pressure, as described above to determine that there is no perforation of the uterine wall.

In FIG. 7A, it can also be seen that the proximal shaft portion 442 of the probe has dimension markings 443 which can be used as an additional safety feature to allow the physician to know the depth of the probe relative to a proximal end 448 of the sealing member 440.

Now turning to FIG. 7B, another scenario is illustrated wherein the probe 400 penetrates the fundus 268 of the uterus. This potential scenario is similar to that of FIG. 6B above wherein the energy applicator 115 of the device penetrated the fundus. In FIG. 7B, it can be seen that $CO_2$ gas will flow outwardly from distal outlets 422a and 422b into the patient's abdominal cavity 270 which offers no resistance to such a gas flow. In this situation, the controller 115 again will monitor flow parameters such as fluid flow rate and fluid pressure in the uterine cavity and will determine whether a perforation exists. More in particular, the flow rate will not drop below a threshold level over a selected time interval which then characterizes the uterus as perforated. Alternatively, the controller 115 can monitor pressure in flow channel 415 to determine that a predetermined threshold pressure is not achieved, which again would indicate that the uterus is perforated.

FIG. 7C illustrates the subsequent step of the ablation procedure wherein the measurement probe 400 is withdrawn from the cervical seal 440, and an ablation device 450 with energy applicator portion 455 is introduced through the cervical seal and the uterine cavity. Thereafter, the energy applicator is activated to complete the ablation procedure as described above. The energy applicator can be of the type described above that also includes flow channels with $CO_2$ inflows to ensure that the ablation device does not penetrate the uterine wall.

Figure 8:
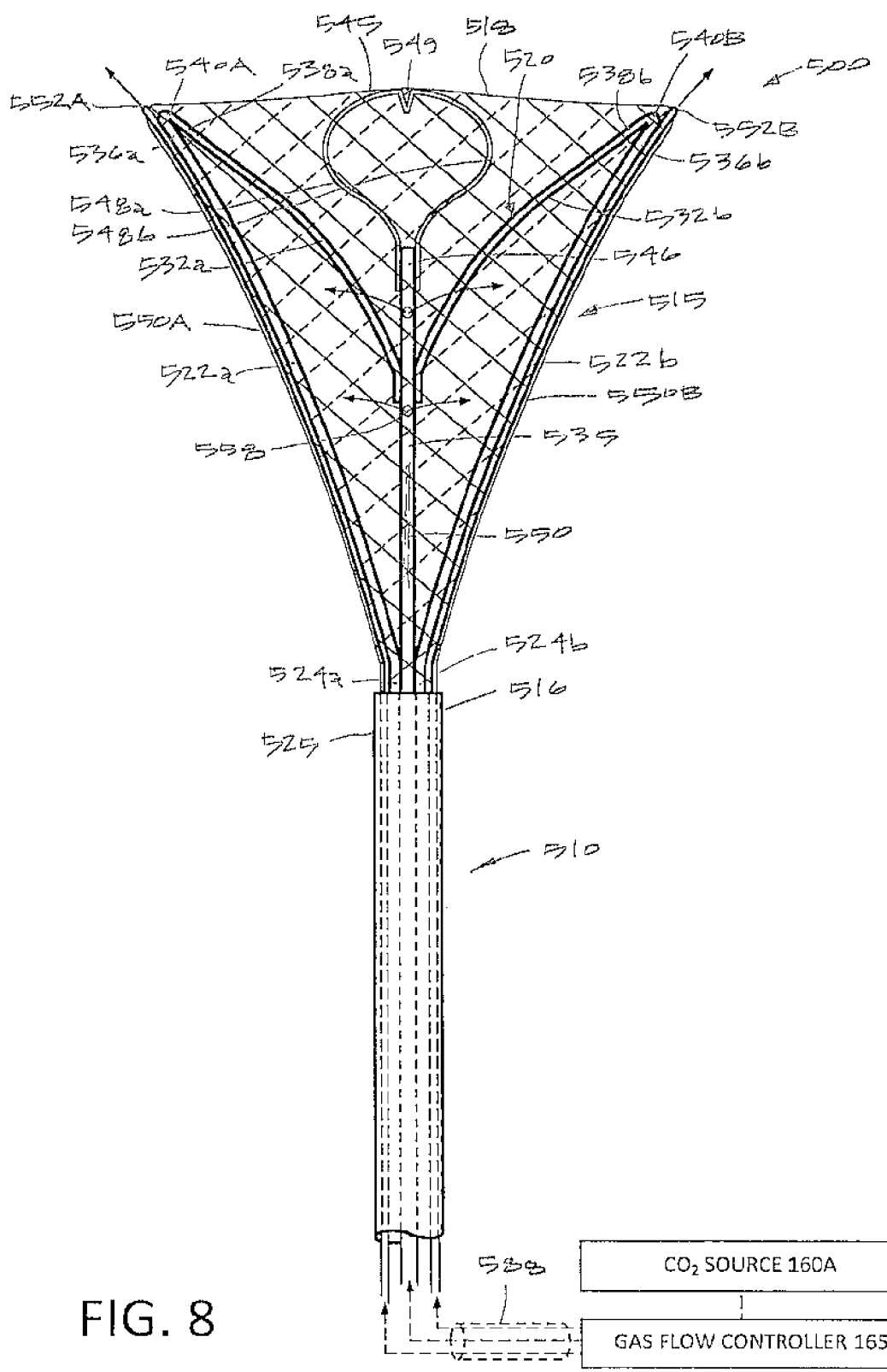
FIG. 8 is a schematic view of a working end of an alternative ablation treatment device wherein the energy applicator portion comprises an expandable elastic, compliant knit structure including flow channels having distal apexes and extending along sides of dielectric structure.
Figure 9:
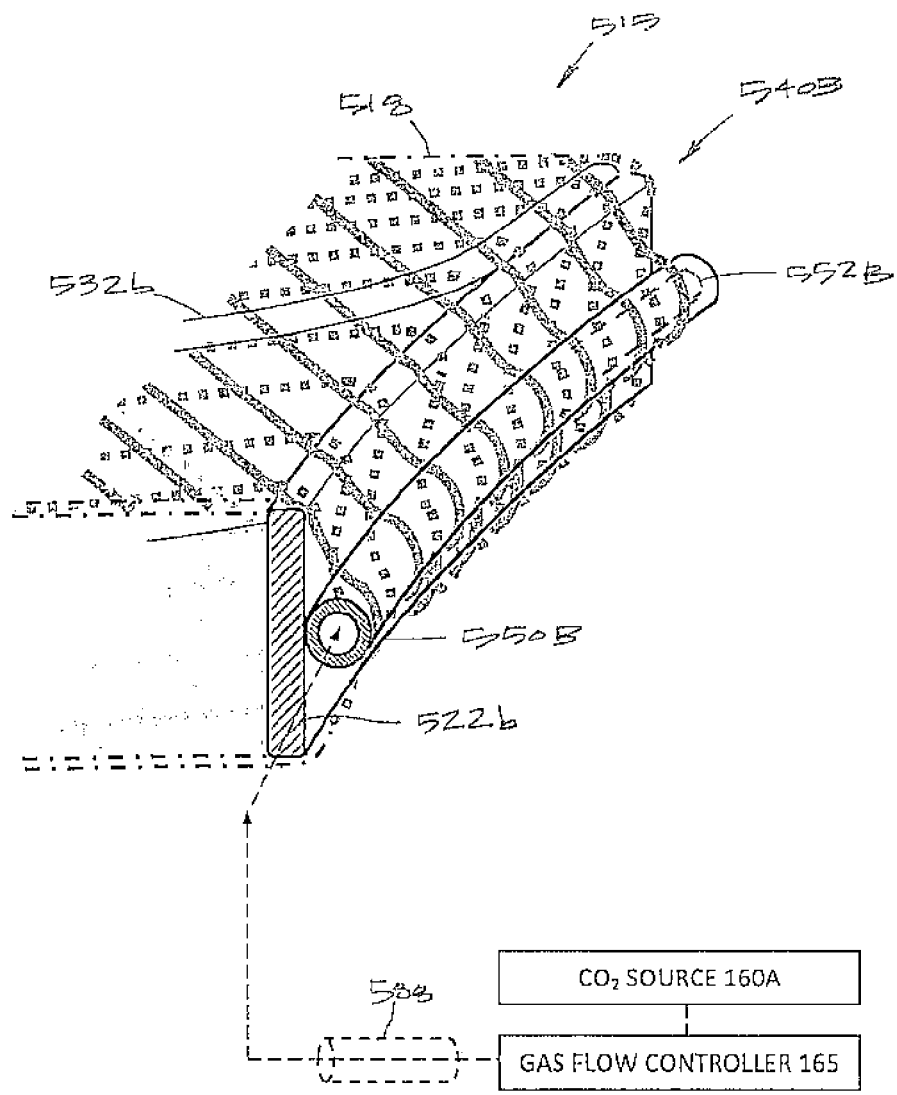
FIG. 9 is an enlarged cut-away perspective view of a distal apex of the applicator body, the knit structure and the flow channel of FIG. 8.

FIGS. 8 and 9 illustrate another embodiment of a working end 500 of an endometrial ablation device which again includes an elongate shaft 510 that carries an expandable-collapsible energy applicator 515 at a distal end 516 of the shaft 510. In this variation, the energy applicator 515 can comprise an expandable, elastic knit structure 518 that carries an electrode arrangement (not shown) which can be of the type disclosed in U.S. Pat. Nos. 5,769,880, 6,813,520 and 6,508,815. The electrode arrangement can be mono-polar or bi-polar. The electrodes carried by the knit structure 518 can comprise conductive metalized yarns, conductive filaments wrapped around elastic yarns or yarns embedded with conductive particles. In one variation, the knit structure 518 comprises a stretchable knit that is similar to a nylon stocking that includes opposing polarity electrode portions spaced apart by dielectric portions as disclosed in in U.S. Pat. Nos. 5,769,880, 6,813,520 and 6,508,815. The working end 500 can be coupled to a motorized handle of the type shown in FIG. 1 or can be used with the types of handles disclosed in U.S. Pat. Nos. 5,769,880, 6,813,520 and 6,508,815. The shaft 510 also can carry an expandable cervical seal as shown in the variations of FIGS. 2 and 6A-7C, which is not shown in FIGS. 8, 10 and 11. In other variations, the sealing member for preventing fluid outflows from the uterine cavity through the endocervical canal can include any form of plug or sealing member known in the art for plugging the external os or the internal os of the cervix.

In the embodiment of FIG. 8, it can be seen that the energy applicator body 515 is expanded by a frame 520 that includes outer flexible elements 522a and 522b with respective proximal ends 524a and 524b that are coupled to an outer sleeve 525. Inner flexible elements 532a and 532b with respective proximal ends 534a and 534b are coupled to an axially moveable inner sleeve 535. The inner and outer flexible elements 522a and 532a have distal tips 536a and 538a on a first side of the frame 520 that are welded or otherwise fixed to each another at a first distal apex 540A. Similarly, the inner and outer flexible elements 522b and 532b have distal tips 536b and 538b on a second side of frame 520 that are fixed to another at a second distal apex 540B. Another expandable-collapsible flexible member 545 is fixed or welded to the distal end 546 of inner sleeve 535. In one variation, the flexible member 545 can comprise a bi-lateral arrangement of thin spring-like flexible portions or elements 548a and 548b that join at the distal end 549 of the member 545. All the flexible elements can comprise a form of stainless steel or similar material. It can be understood that the frame 520 of FIG. 8 can have an arrangement of bi-lateral flexible elements that is similar to the frame elements in the embodiment shown in FIGS. 1-3 above.

In the variation shown in FIG. 8, it can be understood that axial translation of inner sleeve 535 in the distal direction relative to outer sleeve 525 will actuate the flexible elements 522a, 522b, 532a, 532b and 545 to thereby expand the elastic knit structure 518 to a range of triangular shapes, with one such triangular shape shown in FIG. 8. The stretchable knit structure 518 allows for moisture transport through the structure to lumen 550 of the inner sleeve 535 during an ablation procedure when a negative pressure or vacuum source 170 (see FIG. 1) is connected to lumen 550 of inner sleeve 535. The system thus allows for removal of liquid and moisture from a uterine cavity during delivery of RF energy from the electrode arrangement carried by the knit structure 518. Such moisture in the uterine cavity results from an ablation treatment which releases fluid from the uterine wall tissue. If the moisture were not removed, the electrode arrangement typically would not be effective in delivering sufficient RF energy through any such accumulated fluid to the targeted uterine tissue.

In the variation shown in FIG. 8, the working end 500 has flow channels or pathways to provide gas flows through the working end to detect perforations in the uterine wall, which in some variations are similar to such flow channels described in previous embodiments and illustrated in FIG. 6B. More in particular, the energy applicator 515 of FIG. 8 carries fluid flow channel tubing or sleeves 550A and 550B along outward or lateral sides of the triangular shaped energy applicator 515, which is similar to the variations shown in FIGS. 2-4 above. As can be seen in FIGS. 8-9, the flow channel tubing 550A extends to first apex 540A and tubing 550B extends to second distal apex 540B with each tubing having at least one flow outlet 552A, 552B in its distal end proximate to each distal apex of the energy applicator 515. Each flow channel tubing 550A, 550B is in communication with gas source 160A and gas flow controller 165, first shown in the embodiments of FIGS. 1 and 4. In the variation shown in FIG. 8, the gas source 160A is also connected through the handle to the inner sleeve 535 which provides gas flows outward from the open ended lumen 550 of the inner sleeve 535. Further, the gas flow in inner sleeve 535 can exit one or more ports or outlets 558 along the length of sleeve 535 within the interior of energy applicator 515.

FIG. 9 is an enlarged view of flow channel tubing 550B and the second distal apex 540B of the energy applicator 515. The flow tubing 550B can be bonded to, or integrated into, flexible element 522b in any of the manners shown in the variations of FIGS. 3A-3C. Alternatively, the flow tubing 550A, 550B can be floating relative to the adjacent flexible elements 522a, 522b and maintained in place by the elastic knit structure 518.

In a method of use, the shaft 510 and energy applicator 515 can be introduced into a patient's uterine cavity 224 as described previously and the energy applicator 515 can be expanded to a suitable triangular shape to contact the walls of the uterine cavity. Thereafter, gas flows from gas source 160A are provided through fluid flow pathways described above, including through the bilateral gas flow channel tubing 550A and 550B as well as through the inner sleeve 535. If the energy applicator 515 is fully within the uterine cavity 224, then the gas flow controller 165 can monitor flow parameters as described above, such as fluid flow rate and/or fluid pressure in the uterine cavity 224 and can determine that there is no perforation.

Figure 10:
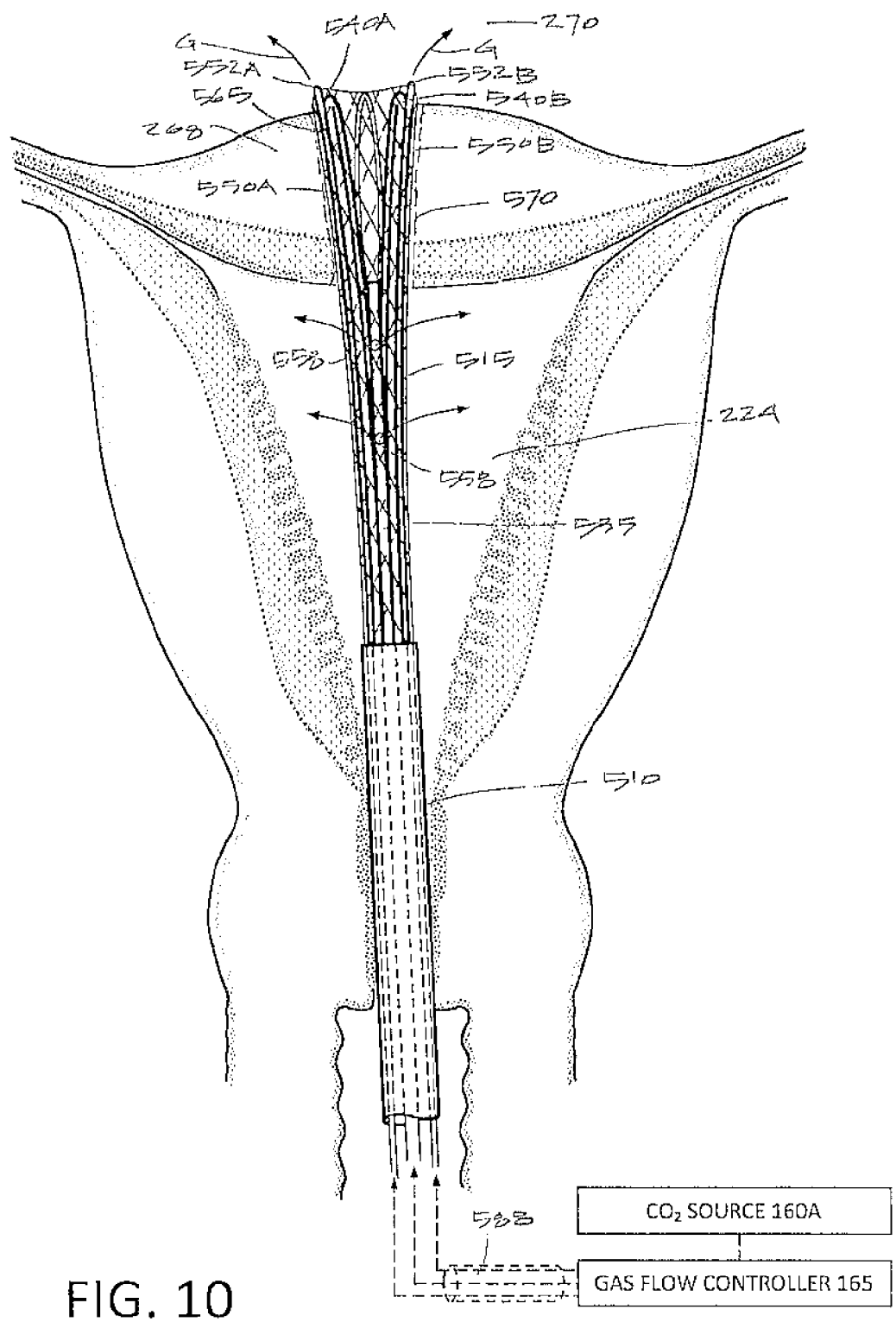
FIG. 10 is a schematic view similar to that of FIG. 6B illustrating the energy applicator of FIGS. 8-9 penetrating the fundus together with gas flows directed though non-collapsible flow channels at each distal apex of the applicator and into the abdominal cavity, wherein monitoring at least one gas flow parameter through the flow channels will determine that there is a perforation in the uterine cavity wall.

Now turning to FIG. 10, a perforation scenario is illustrated which is similar to that of FIG. 6B. In FIG. 10, the distal portion 565 of the energy applicator 515 penetrates the fundus 268 of the uterus which can happen, for example, when a sounding probe creates a perforation 570 and thereafter the collapsed energy applicator 515 follows the same path through the perforation 570. In this situation as shown in FIG. 10, the $CO_2$ gas flows indicated a G flow outwardly from distal outlets 552A and 552B into the patient's abdominal cavity 270 which offers no resistance to such a gas flow. As shown in FIG. 10, $CO_2$ gas also flows into the uterine cavity 224 through inner sleeve 535 and ports 558 therein to fill the cavity. In this case, the gas flow controller 165 again can detect the perforation 570 by monitoring a parameter of the gas flow as described previously, which can be flow-related, pressure related or gas volume related. In one example, if the flow rate does not drop below a threshold level over a selected time interval as described above, then the controller system characterizes the uterus as perforated. If the flow rate does drop below the selected threshold level over a selected time interval, then the controller system characterizes the uterus as non-perforated. As described above in a previous embodiment, the initial flow rate can be between 0.01 slpm and 1.0 slpm. In one variation, the flow rate is between 0.05 slpm and 0.10 slpm. The gas flow controller 165 and flow meter therein then can determine that either (i) the flow rate has dropped to zero or below a threshold level lose to thus characterize the uterine cavity as non-perforated, or (ii) the flow rate has not dropped to a predetermined threshold level within a predetermined time interval to thus characterize the uterine cavity as perforated or that there is leakage through the cervical canal. In one variation, the threshold level can be between 0.02 slpm and 0.05 slpm for characterizing the uterine cavity as non-perforated. In this variation, the controller can provide a signal indicating a non-perforated uterine cavity if the flow drops below the threshold level in a pre-determined time interval as described previously. In another variation of the method, the controller can be adapted to repeat the same test at least a second time following the completion of the first test. Optionally, between the first test and a subsequent test, the energy applicator can be adjusted in its position the uterine cavity or can be adjusted in its degree of expansion.

In another alternative, the gas flow controller 165 can monitor pressure in flow channel 588 to determine that a predetermined threshold pressure is not achieved, which again would indicate that the uterus is perforated. As can be seen in FIGS. 8-11, the flow channel 588 extends from the $CO_2$ source 160A and controller 165 to communicate with flow channel tubing 550A and 550B and inner sleeve 535. The controller 165 can be configured to sense pressure in flow channel 588 which thus senses pressure simultaneously through all flow pathways (550A, 550B and 535) or the controller 165 and sensors can be configured to sense pressure in one or more pathways on an individual basis. In a variation, the controller would be adapted to provide a flow rate in the range described previously, and thereafter monitor pressure to determine whether a predetermined pressure, for example between 25 mmHg and 75 mmHg, is achieved and maintained over a predetermined interval which be at least 5 seconds.

Figure 11:
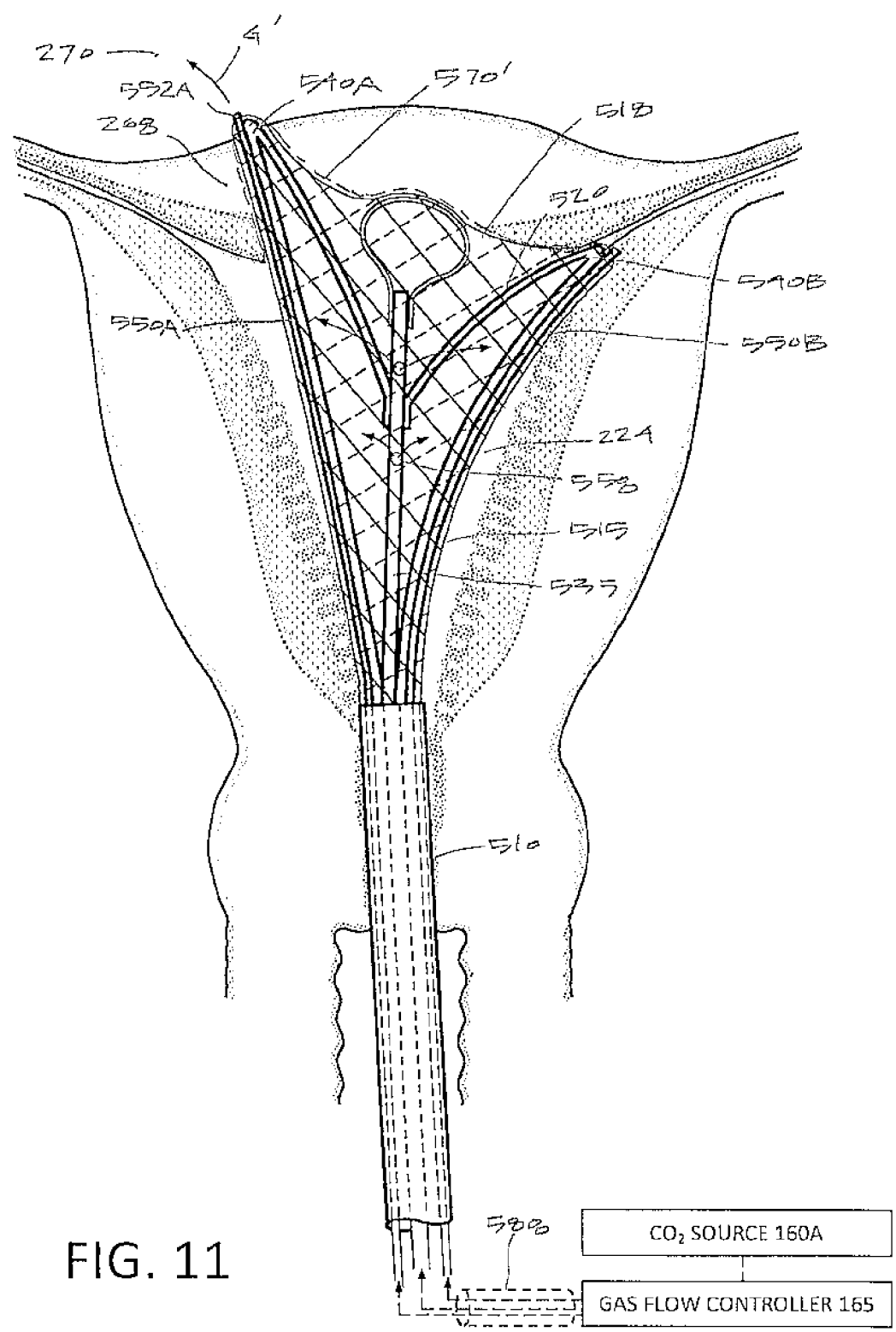
FIG. 11 is a schematic view similar to that of FIG. 10 illustrating one of the two apexes of the energy applicator of FIGS. 8-9 penetrating the fundus together with a gas flow directed though flow channel into the abdominal cavity, which can be monitored by a controller to determine that there is a perforation in the uterine wall.

FIG. 11 illustrates another perforation scenario which has been known to occur. Often, a uterus has an irregular shape, is retroverted or anteverted which can be a factor in a perforation by the deployment or expansion of energy applicator 515. In the example of FIG. 11, the distal apex 540A of the applicator body 515 is caught in endometrial tissue of the fundus 268 after insertion of the device, and thereafter expansion of the energy applicator 515 with the expandable frame 520 can cause the distal apex 540A to dissect or tear tissue and ultimately causes a perforation indicated at 570'. The flexible frame 520 and knit structure 518 can be deformed to an asymmetric shape during expansion if an apex is captured in tissue. As can be seen in FIG. 11, the $CO_2$ gas flow indicated at G' flows outwardly from distal outlet 552A into the patient's abdominal cavity 270. As described previously, the gas flow controller 165 then can detect the perforation 570' by monitoring a parameter of the gas flow from source 160A, which can be a flow-related parameter, a pressure related parameter or gas volume related parameter.

Figure 12:
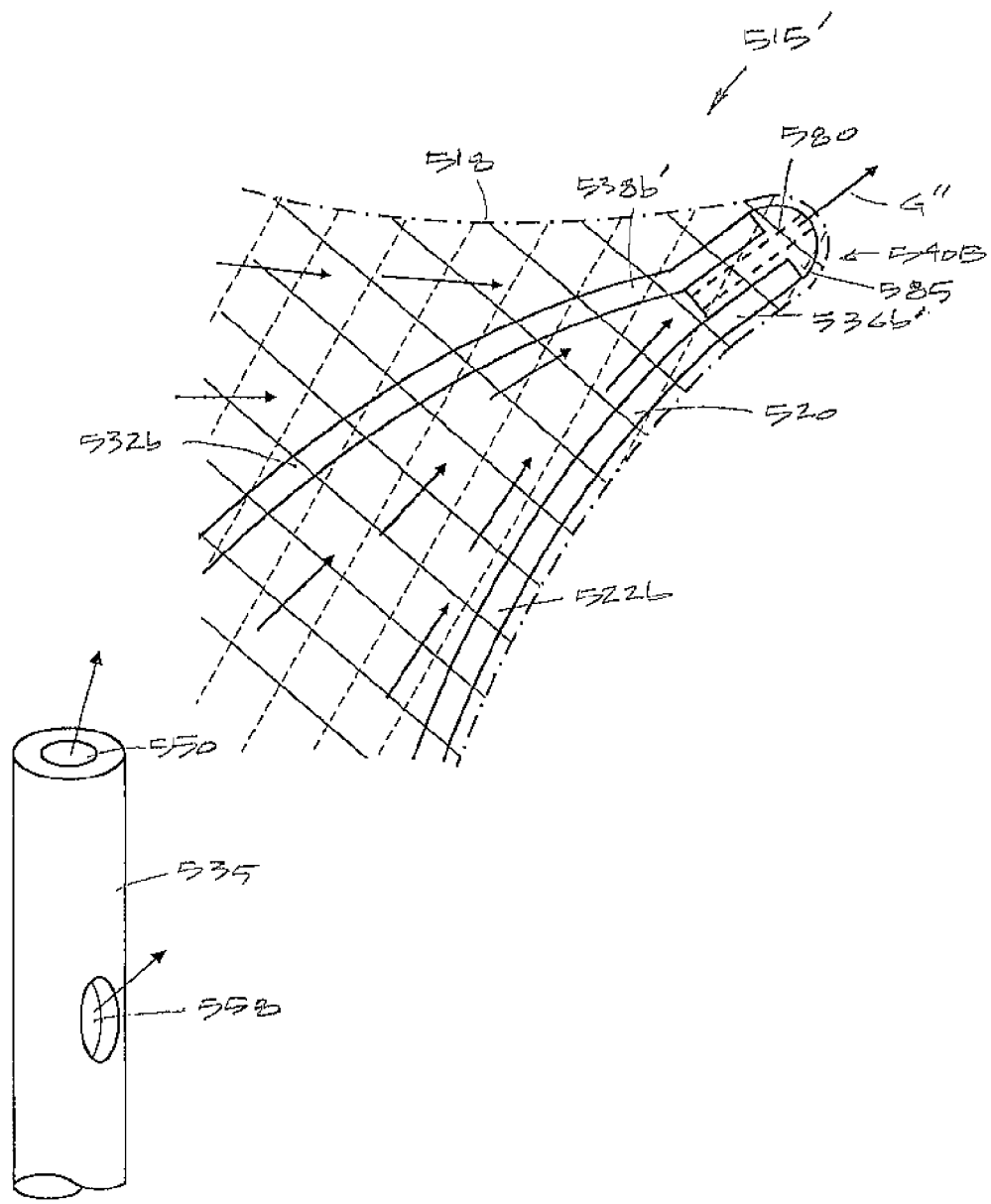
FIG. 12 is an enlarged schematic view of a distal portion of an alternative energy applicator similar to that of FIG. 8 but having a flow channel extending through an apex of the applicator and communicating with an interior of the porous knit structure.

FIG. 12 schematically illustrates a portion of another embodiment of energy applicator 515' that does not utilize the continuous flow channel tubing 550A, 550B as depicted in the embodiment of FIGS. 8-9. In FIG. 12, each distal apex 540A, 540B of the frame 520' has a flow channel 580 extending therethrough. FIG. 12 shows distal apex 540B in an enlarged view where flow channel 580 extends through an interior of connecting portions of the distal tips 536b' and 538b' of the respective flexible elements 522b' and 532b'. In one variation, the distal tips 536b' and 538b' of the flexible elements can be welded or otherwise fixed to tip member 585 with flow channel 580 therein. As can be understood from FIG. 12, $CO_2$ gas flow through the inner sleeve 535 will fill the uterine cavity through the porous knit structure 518 and flow into and through the flow channel 580 and if either apex (or both) 540A, 540B has penetrated through the uterine wall into the abdominal cavity, then the $CO_2$ gas flow indicated at G" in FIG. 12 will cause the gas flow controller 165 to detect the perforation as described previously.

Figure 13:
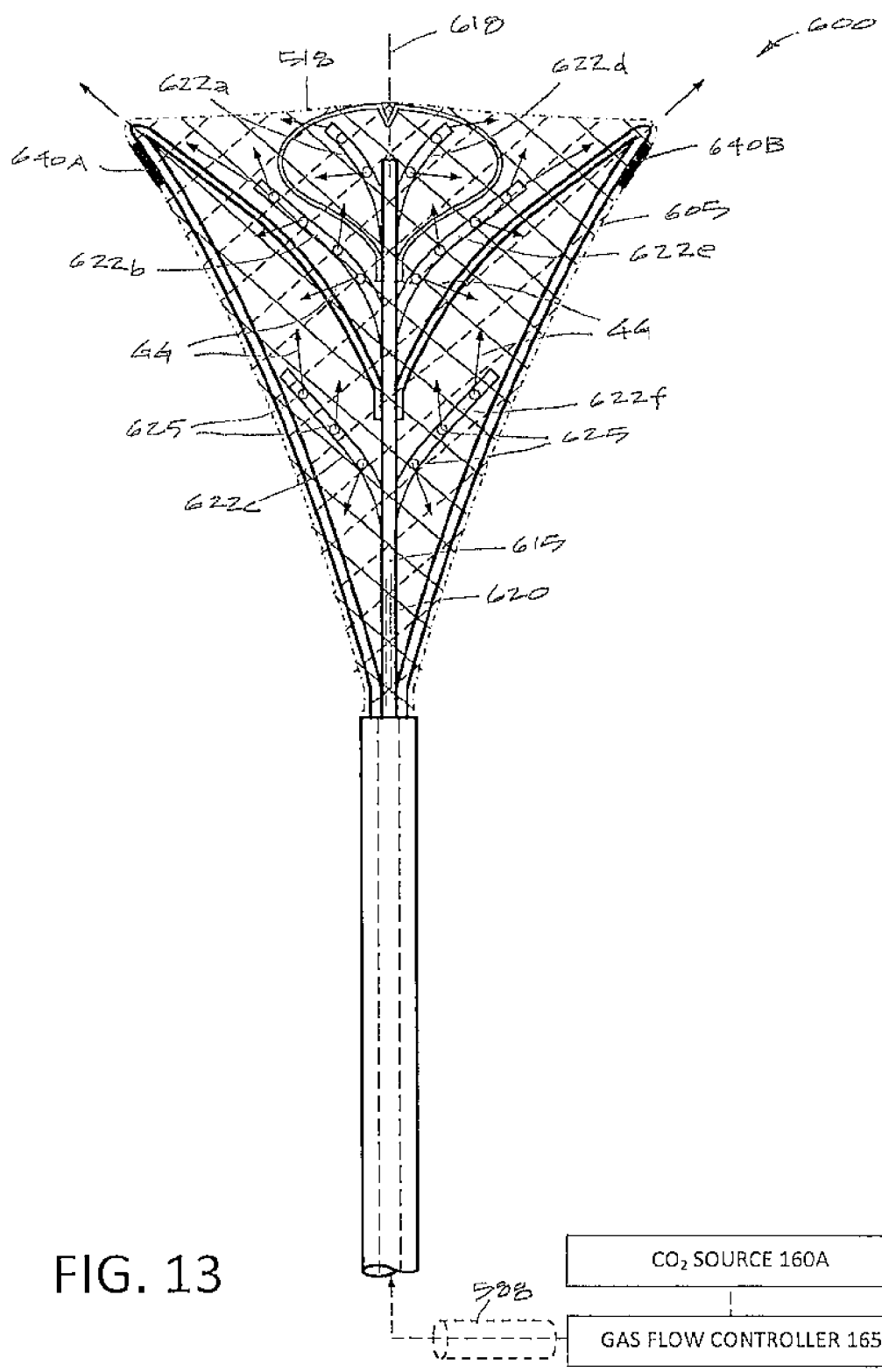
FIG. 13 is a plan view of an alternative working end similar to that of FIG. 8 wherein the energy applicator again comprises an expandable elastic knit structure, but including a plurality including of flow channels and outlets spaced apart from the axis of the applicator and spatially distributed about the interior of the knit structure.

FIG. 13 illustrates another variation of a working end 600 that is similar to that of FIG. 8, except that the energy applicator 605 has a different configuration of flow channels in its interior that communicate with a fluid inflow source 160A and/or a fluid outflow source. As can be seen in FIG. 13, the inner sleeve 615 extends about axis 618 and has a lumen 620 therein that is connected to the gas source 160A and gas flow controller 165. In this variation, the inner sleeve 615 carries a plurality of flexible branches 622a-622f, for example of a thin wall polymer tubing, that are resilient and adapted to branch away from the inner sleeve 615 and axis 618 toward the non-tensioned position of each branch 622a-622f. The branches 622a-622f each have lumens that communicate with the lumen 620 in inner sleeve 615 and the $CO_2$ gas source 160A. Each of branches 622a-622f can have a plurality of outlets 625 along its length with such outlets 625 also having different rotational orientations around each branch. In use, as shown in FIG. 13, the gas inflows indicated by arrows GG then will be introduced into the interior of the knit structure 518' from a plurality of outlets 625 disposed at locations that are dispersed over a wide area within the perimeter of energy applicator 605. As can be seen in FIG. 13, a plurality of the outlets are spaced away from the axis 618 and the inner sleeve 615. The purpose for providing branches 622a-622f in a plurality of dispersed outlets 625 is to ensure that $CO_2$ gas is delivered through the porous knit structure 518' and into the uterine cavity 224 to thereby expand the uterine cavity. In previous embodiments, the $CO_2$ gas inflows typically flowed from a single lumen or from the flow channel outlets along axis 618 of the energy applicator 605. Thus, it was possible that blood, detached endometrial tissue, and viscous fluids could block the limited number of outlets along the axis of the applicator 605. It can be understood that if such outlets were blocked, the gas flow controller 165 would not be able to properly detect perforations in the uterine wall. Therefore, it has been found important to distribute the gas inflow outlets 625 over the interior of the knit structure 518'.

Other means of distributing $CO_2$ gas inflows about the energy applicator, or away from axis 618 in FIG. 13, can include using tubular elements in the knit structure 518' where each such tubular element is coupled to the $CO_2$ gas source. Alternatively, a thin foldable polymer membrane, such as a mylar film, with a triangular shape may be carried on one side of the frame and in the interior of the knit structure. The mylar film may have flow channels therein that communicate with porosities in the film or outlets spaced about the surface of the mylar. Such a non-conductive mylar film is further useful in that it can provide an insulator layer between opposite sides of the knit structure 518' that may carry opposing polarity bipolar electrodes.

In another aspect of the invention, still referring to FIG. 13, the outlets 625 and branches 622a-622f can be similarly useful during an ablation procedure when a negative pressure source is coupled to the lumen 620 of the inner sleeve 615 and the lumens of the branches 622a-622f. Again, blood and tissue may become attached to the surface of the knit structure 518 and block the outflow of fluid and moisture through the knit structure 518' and into inner sleeve 615. Thus, it can be understood that it is desirable to have such aspiration outlets 625 spaced apart and distributed over the interior of the energy applicator 605.

In another aspect of the invention, referring again to FIG. 13, ultrasound transducers 640A and 640B can be carried near each distal apex of the energy applicator 605. Such ultrasound transducers can be positioned at any suitable location on the inner or outer flexible elements or can be carried by the knit structure 518'. The ultrasound transducers 640A and 640B can be operatively connected to a controller that uses signals from the transducers to provide an image on a display, or other signals, that can indicate to the physician whether a perforation exists in the uterine wall.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for positioning an expandable-collapsible energy applicator in a uterine cavity of the patient, said method comprising:
    introducing an elongated shaft carrying said expandable-collapsible energy applicator through a cervix of the patient into the uterine cavity, said expandable-collapsible energy applicator comprising an energy applicator body;
    actuating a frame within the energy applicator body to expand the energy applicator body to a triangular shape within the uterine cavity with a first distal apex and a second distal apex;
    introducing a fluid flow through tubing in or on the energy applicator body, wherein the fluid flow is released through a first distal outlet at the first distal apex and a second distal outlet at the second distal apex during or after introduction of the elongated shaft through the cervix;
    monitoring at least one parameter of the fluid flow through the tubing to detect a perforation in a uterus of the patient, wherein the at least one parameter is selected from the group consisting of fluid flow rate, fluid pressure, and fluid flow volume.

2. The method of claim 1 further comprising sealing the cervix with a sealing member prior to or while introducing the fluid flow to prevent fluid loss through the cervix.

3. The method of claim 1 wherein the fluid flow introducing step includes utilizing a controller to control and/or monitor the fluid flow.

4. The method of claim 3 wherein the controller is configured to control the fluid flow at a rate of between 0.01 slpm and 1.0 slpm.

5. The method of claim 1 wherein the monitoring step includes determining if the fluid flow rate drops below a predetermined minimum threshold level over a predetermined time interval after initiation of the fluid flow to thereby characterize the uterus as not perforated.

6. The method of claim 5 wherein the predetermined minimum threshold level is between 0.02 slpm and 0.05 slpm.

7. The method of claim 5 wherein the predetermined time interval is between 1 second and 20 seconds.

8. The method of claim 5 wherein the monitoring step further includes determining if the fluid flow rate does not drop below the predetermined threshold minimum level over the predetermined time interval after initiation of the fluid flow to thereby characterize the uterus as perforated.

9. The method of claim 1 wherein the monitoring step includes determining if a monitored pressure remains above a predetermined threshold pressure level for a predetermined time interval to characterize the uterus as not perforated.

10. The method of claim 9 wherein the predetermined threshold pressure level is between 25 mmHg and 75 mmHg and the predetermined time interval is at least 5 seconds.

11. The method of claim 10 wherein the monitoring step includes determining if the monitored pressure does not remain above the predetermined threshold pressure level for the predetermined time interval to characterize the uterus as perforated.

12. The method of claim 1 wherein the tubing includes a first tube having the first distal outlet at a distal tip of the first tube and a second tube having the second distal outlet at a distal tip of the second tube.

13. The method of claim 12 further comprising introducing the fluid flow through ports disposed along lengths of the first tube and the second tube while the elongated shaft is being introduced through the cervix.

14. The method of claim 1 wherein the frame is actuated to expand the energy applicator in the uterine cavity prior to or while monitoring the at least one parameter of the fluid flow.

15. The method of claim 1 wherein the fluid flow comprises $CO_2$.

16. The method of claim 1 wherein the fluid flow introducing and the at least one parameter monitoring steps are repeated at least twice in sequence.

17. The method of claim 1 wherein when the uterus is characterized as not being perforated, further comprising activating the expandable-collapsible energy applicator in response to the uterus being characterized as not perforated.

18. The method of claim 1 wherein when the uterus is characterized as being perforated, further comprising actuating a lock-out adapted to prevent activation of the expandable-collapsible energy applicator.

19. The method of claim 2 wherein the sealing member is disposed in at least one of the cervix, an external os of the patient and an internal os of the patient.

20. The method of claim 1 wherein the energy applicator body comprises an expandable, elastic knit structure that carries an electrode arrangement.

\* \* \* \* \*